US007674953B2

(12) United States Patent
Mulet Salort et al.

(10) Patent No.: US 7,674,953 B2
(45) Date of Patent: Mar. 9, 2010

(54) **METHOD FOR PRODUCING TRANSGENIC PLANTS WITH INCREASED YIELD, COMPRISING EXPRESSING OF HAEMOGLOBIN FROM *ARABIDOPSIS***

(75) Inventors: Jose Miguel Mulet Salort, Basel (CH); Ana Isabel Sanz Molinero, Gentbrugge (BE); Ramon Serrano Salom, Valencia (ES)

(73) Assignee: Cropdesign N.V., Zwijnaarde (BE)

( * ) Notice: Subject to any disclaimer, the term of this patent is extended or adjusted under 35 U.S.C. 154(b) by 0 days.

(21) Appl. No.: 10/551,699

(22) PCT Filed: Apr. 1, 2004

(86) PCT No.: PCT/EP2004/050405

§ 371 (c)(1),
(2), (4) Date: Nov. 21, 2005

(87) PCT Pub. No.: WO2004/087755

PCT Pub. Date: Oct. 14, 2004

(65) Prior Publication Data

US 2006/0288455 A1 Dec. 21, 2006

(30) Foreign Application Priority Data

Apr. 1, 2003 (EP) .................................. 03075974

(51) Int. Cl.
*C12N 15/82* (2006.01)
*A01H 5/00* (2006.01)

(52) U.S. Cl. ...................... 800/290; 800/278; 435/468

(58) Field of Classification Search ...................... None
See application file for complete search history.

(56) References Cited

U.S. PATENT DOCUMENTS 5,959,187 A * 9/1999 Bailey et al. ............. 800/317.3
6,372,961 B1 4/2002 Tarczynski et al.

FOREIGN PATENT DOCUMENTS

| EP | 1033405 A2 * | 6/2000 |
| WO | 98/12913 A | 4/1998 |
| WO | 00/00597 A | 1/2000 |
| WO | 02/16655 A | 2/2002 |
| WO | 2004/057946 A | 7/2004 |

OTHER PUBLICATIONS

Town et al. (NCBI, GenBank, Sequence Accession No. NM_111887, Published Aug. 20, 2002).*
Hunt et al. (Plant Molecular Biology, 47:677-692, 2001, Applicant's IDS).*
Dordas et al. (Annals of Botany, 91:173-178, 2003).*
Trevaskis et al. (NCBI, GenBank Sequence Accession No. U94999, Published Nov. 6, 1997).*
Town et al. *Arabidopsis thaliana* chromosome 3 CHR3v12152001 genomic sequence. (2002) GenBank Accession NM_111887; pp. 1-2.*
International Search Report of PCT/EP2004/050405, mailed Dec. 22, 2004.
De Los Reyes et al., "SB48 Sugar Beet germination cDNA library Beta vulgaris cDNA clone ys016149 5' similar to a class 2 non-symbiotic hemoglobin, mRNA sequence.", Database EM Est, Aug. 18, 2000, XP002295394, Database accession No. BE590299.
Herwig et al., "E012352-024-011-H14-SP6 MPIZ-ADIS-024-leaf Beta vulgaris cDNA clone 024-011-H14 5-PRIME, mRNA sequence", XP002252725, Database accession No. BQ586966.
Trevaskis et al., "Two Hemoglobin Genes in *Arabidopsis thaliana*: The Evolutionary Orgins of Leghemoglobins", Proceedings of the National Academy of Sciences of USA, National Academy of Science, Vol. 94, Oct. 1997, pp. 12230-12234, XP002117102.
Hunt et al., "Expression and evolution of functionally distint haemoglobin genes in plants", Plant Molecular Biology, vol. 47, No. 5, Nov. 2001, pp. 677-692, XP002295393.
Hunt et al, "Expression and evolution of functionally distinct haemoglobin genes in plants", Plant Molecular Biology 47:677-692, 2001.
Bulow et al "The metabolic effects of native and transgenic hemoglobins on plants" TIBTECH, Jan. 1999, vol. 17, 21-24.

* cited by examiner

*Primary Examiner*—Cathy Kingdon Worley
(74) *Attorney, Agent, or Firm*—Nixon & Vanderhye P.C.

(57) ABSTRACT

The invention relates generally to a method for improving growth of plants, under normal and under stress conditions, more particularly under osmotic stress and/or temperature extremes, comprising modifying plant haemoglobin gene expression and/or by modifying plant haemoglobin protein levels in a plant. The invention furthermore relates to a method for increasing yield of a plant, comprising modifying plant gene expression and/or by modifying plant haemoglobin levels in a plant. The invention also relates to a nucleic acid encoding a haemoglobin conferring this altered growth and stress tolerance.

2 Claims, 6 Drawing Sheets

```
Name:  at               Len:   162  Check:  5339  Weight:   1.00
Name:  bn               Len:   162  Check:  8426  Weight:   1.00
Name:  bv               Len:   162  Check:  6644  Weight:   1.00
Name:  gh               Len:   162  Check:  7625  Weight:   1.00
Name:  le               Len:   162  Check:  951   Weight:   1.00
Name:  cg               Len:   162  Check:  1715  Weight:   1.00

//

1                                                          50
at    MGEIGFTEKQ  EALVKESWEI  LKQDIPKYSL  HFFSQILEIA  PAAKGLFSFL
bn    mgeivftekq  ealvkeswei  lkqdipkysl  hffsqileia  paakdmfsfl
bv    ---MTFTEKD  EALVKESWDI  MKQNIPEYSL  RFFSIILEIA  PAAKNMFSFL
gh    ---mgftekq  eglvkeswev  lkqdiphssl  rffslileia  pgaknmfsfl
le    ---mgftdkq  ealvrdswef  mkqdipqlsl  rffslileia  pvaknmfsfl
cg    ---maltekq  eallkqswev  lkqnipahsl  rlfalileaa  peskyvfsfl 51                                                         100
at    RDSDEVPHNN  PKLKAHAVKV  FKMTCETAIQ  LREEGKVVVA  DTTLQYLGSI
bn    rdtdevphnn  pklkahavkv  fkmtcetaiq  lrekgkvvva  dttlqylgsv
bv    RDSEEVPQNN  PKLKAHAIKV  FKMTCESAIQ  LREKGEVVVG  ETTLKYLGAI
gh    reseeipqnn  pklkahavkv  fkmtcesaiq  lrekgevvva  dttlkylgtv
le    kdsdelpenn  pklrahavkv  fkmtcesaiq  lrekgevvvg  ettlkylgsi
cg    kdsneipenn  pklkahaavi  fkticesate  lrqkghavwd  nntlkrlgsi 101                                                        150
at    HLKSGVIDPH  FEVVKEALLR  TLKEGLG.EK  YNEEVEGAWS  QAYDHLALAI
bn    hfksgvldph  fevvkealvr  tlkeglg.ek  yneevegaws  kaydhlalai
bv    HLKNGVIDPH  FEVVKQALLR  TIEEASG.DK  WSEELKCAWS  VAYDHLAAAI
gh    hvksgvkdph  fevvkeallr  tieeaigeek  wneemknawg  eaydqlaeai
le    hlqkrvadph  fevvkeallr  tvkeatg.nk  wkdemkeaws  eaydqlasai
cg    hlknkitdph  fevmkgallg  tikeai.ken  wsdemgcawt  eaynqlvati 151         162
at    KTEMKQEES-  --
bn    kaemkqedsq  kp
bv    KAEMKE*---  --
gh    kaemknhhde  ta
le    kaemhaeaaa  --
cg    kaemke----  --
```

FIGURE 1

SEQUENCE LISTING

```
<160> NUMBER OF SEQ ID NOS: 21

<210> SEQ ID NO 1
<211> LENGTH: 860
<212> TYPE: DNA
<213> ORGANISM: Beta vulgaris

<400> SEQUENCE: 1
tacaaaccac aaatttaagc tattaataca ctttctctgt cattttttgt tgttccaatt      60
tagtttcttt tcttttaaat taaaacaaaa ctatgacttt tacagagaaa gatgaagctt     120
tggtaaaaga atcatgggat ataatgaagc aaaatatccc agaatacagc cttcggtttt     180
tctccataat attggaaatt gctccagcag ccaaaaatat gttctcattt ttaagggatt     240
```

```
cagaggaagt tccacagaat aatcccaagc tgaaagctca tgcaatcaag gttttaaaa      300 tgacatgtga atcagccatt caacttcgag aaaaaggtga agtggttgta ggagagacta     360
cccttaaata tttgggagct atccatttga agaatggagt gattgatccc cattttgagg     420
ttgtgaaaca agcattattg agaaccatag aagaagcaag tggtgacaaa tggagtgaag     480
aattgaaatg tgcttggagt gttgcctatg atcacttagc tgcagccatc aaagctgaga     540
tgaaggaata ggtagcttag ttctcagtcg ccaaaagtat tactctaaaa atattgaata     600
aatattctta ttgttttga ggggaaatta ttgttattgt tgattctgac tcacttattt      660
atccgagtga cttgatatgg tgcttttcct tgccttatta ttgattagca agaaggaaat    720
caaattcata attattggtt taaccatgta atagtgcata ttaattgtga taaaaccttg    780
gtgatatatg taccttattg caaatttaaa ataatattcc ctcggtcttt cattttaaaa    840
aaaaaaaaaa aaaaaaaaa                                                  860

<210> SEQ ID NO 2
<211> LENGTH: 152
<212> TYPE: PRT
<213> ORGANISM: Beta vulgaris

<400> SEQUENCE: 2

Met Thr Phe Thr Glu Lys Asp Glu Ala Leu Val Lys Glu Ser Trp Asp
1               5                  10                  15

Ile Met Lys Gln Asn Ile Pro Glu Tyr Ser Leu Arg Phe Phe Ser Ile
            20                  25                  30

Ile Leu Glu Ile Ala Pro Ala Ala Lys Asn Met Phe Ser Phe Leu Arg
        35                  40                  45

Asp Ser Glu Glu Val Pro Gln Asn Asn Pro Lys Leu Lys Ala His Ala
    50                  55                  60

Ile Lys Val Phe Lys Met Thr Cys Glu Ser Ala Ile Gln Leu Arg Glu
65                  70                  75                  80

Lys Gly Glu Val Val Val Gly Glu Thr Thr Leu Lys Tyr Leu Gly Ala
                85                  90                  95

Ile His Leu Lys Asn Gly Val Ile Asp Pro His Phe Glu Val Val Lys
            100                 105                 110

Gln Ala Leu Leu Arg Thr Ile Glu Glu Ala Ser Gly Asp Lys Trp Ser
        115                 120                 125

Glu Glu Leu Lys Cys Ala Trp Ser Val Ala Tyr Asp His Leu Ala Ala
    130                 135                 140

Ala Ile Lys Ala Glu Met Lys Glu
145                 150

<210> SEQ ID NO 3
<211> LENGTH: 858
<212> TYPE: DNA
<213> ORGANISM: Arabidopsis thaliana

<400> SEQUENCE: 3
attgaatacc atatatatat agatacacag acatataaac acacaaatat tcgtgttttt     60
ttcaaactgt gagagaaaaa gaaagagaga aagagatggg agagattggg tttacagaga    120
agcaagaagc tttggtgaag gaatcgtggg agatactgaa acaagacatc cccaaataca    180
gccttcactt cttctcacag atactggaga tagcaccagc agcaaaaggc ttgttctctt    240
tcctaagaga ctcagatgaa gtccctcaca acaatcctaa actcaaagct catgctgtta    300
aagtcttcaa gatgacatgt gaaacagcta tacagctgag ggaggaagga aaggtggtag    360
```

-continued

```
tggctgacac aaccctccaa tatttaggct caattcatct caaaagcggc gttattgacc    420
ctcacttcga ggtggtgaaa gaagctttgc taaggacatt gaaagagggg ttgggggaga    480
aatacaatga agaagtggaa ggtgcttggt ctcaagctta tgatcacttg gctttagcca    540
tcaagaccga gatgaaacaa gaagagtcat aaaaccctat tgatcatttg ggtatcgcat    600
acatgaatct attccacata catgatacac atatacgtgt ttctgtgtgt gtactatgtt    660
gctctctgac tttctacagt tcactatttt aattataaag aaggatcttg tgctatcatt    720
agggagatac gtgatactgt agttcttctt gaaattgtta ttcgtgagaa atatcatggt    780
ttgaagtatt tattttcaca agatggatgt taacgtgggg atcattttac aatcattcta    840
caaataattt tacttctc                                                   858
```

<210> SEQ ID NO 4
<211> LENGTH: 158
<212> TYPE: PRT
<213> ORGANISM: Arabidopsis thaliana

<400> SEQUENCE: 4

```
Met Gly Glu Ile Gly Phe Thr Glu Lys Gln Glu Ala Leu Val Lys Glu
1               5                   10                  15
Ser Trp Glu Ile Leu Lys Gln Asp Ile Pro Lys Tyr Ser Leu His Phe
            20                  25                  30
Phe Ser Gln Ile Leu Glu Ile Ala Pro Ala Ala Lys Gly Leu Phe Ser
        35                  40                  45
Phe Leu Arg Asp Ser Asp Glu Val Pro His Asn Asn Pro Lys Leu Lys
    50                  55                  60
Ala His Ala Val Lys Val Phe Lys Met Thr Cys Glu Thr Ala Ile Gln
65                  70                  75                  80
Leu Arg Glu Glu Gly Lys Val Val Val Ala Asp Thr Thr Leu Gln Tyr
                85                  90                  95
Leu Gly Ser Ile His Leu Lys Ser Gly Val Ile Asp Pro His Phe Glu
            100                 105                 110
Val Val Lys Glu Ala Leu Leu Arg Thr Leu Lys Glu Gly Leu Gly Glu
        115                 120                 125
Lys Tyr Asn Glu Glu Val Glu Gly Ala Trp Ser Gln Ala Tyr Asp His
    130                 135                 140
Leu Ala Leu Ala Ile Lys Thr Glu Met Lys Gln Glu Glu Ser
145                 150                 155
```

<210> SEQ ID NO 5
<211> LENGTH: 486
<212> TYPE: DNA
<213> ORGANISM: Brassica napus

<400> SEQUENCE: 5

```
atgggagaga ttgtgtttac ggagaagcaa gaagctttgg tgaaggagtc ttgggagata     60
ctaaagcaag atatcccaa atacagtctt cacttcttct cacagatact ggagatagca    120
ccagcagcaa aggacatgtt ctctttccta agagacacag atgaagtccc tcataacaat    180
cctaaactca agctcatgc tgttaaagtc ttcaagatga catgtgagac agcaatacag    240
ctgagggaga aaggaaaggt agtggtggct gacacaaccc tccaatactt gggctctgtt    300
catttcaaga gcggtgttct tgatcctcac tttgaggtgg tgaaagaggc attggtgagg    360
acactgaaag aagggttggg ggagaagtac aatgaagaag tggaaggagc ttggtccaag    420
```

-continued

```
gcttatgatc acttggcttt agccattaag gccgagatga acaagaaga ctcacaaaaa    480 ccctaa                                                              486
```

<210> SEQ ID NO 6
<211> LENGTH: 161
<212> TYPE: PRT
<213> ORGANISM: Brassica napus

<400> SEQUENCE: 6

Met Gly Glu Ile Val Phe Thr Glu Lys Gln Glu Ala Leu Val Lys Glu
1               5                   10                  15

Ser Trp Glu Ile Leu Lys Gln Asp Ile Pro Lys Tyr Ser Leu His Phe
            20                  25                  30

Phe Ser Gln Ile Leu Glu Ile Ala Pro Ala Ala Lys Asp Met Phe Ser
        35                  40                  45

Phe Leu Arg Asp Thr Asp Glu Val Pro His Asn Asn Pro Lys Leu Lys
    50                  55                  60

Ala His Ala Val Lys Val Phe Lys Met Thr Cys Glu Thr Ala Ile Gln
65                  70                  75                  80

Leu Arg Glu Lys Gly Lys Val Val Val Ala Asp Thr Thr Leu Gln Tyr
                85                  90                  95

Leu Gly Ser Val His Phe Lys Ser Gly Val Leu Asp Pro His Phe Glu
            100                 105                 110

Val Val Lys Glu Ala Leu Val Arg Thr Leu Lys Glu Gly Leu Gly Glu
        115                 120                 125

Lys Tyr Asn Glu Glu Val Glu Gly Ala Trp Ser Lys Ala Tyr Asp His
    130                 135                 140

Leu Ala Leu Ala Ile Lys Ala Glu Met Lys Gln Glu Asp Ser Gln Lys
145                 150                 155                 160

Pro

<210> SEQ ID NO 7
<211> LENGTH: 50
<212> TYPE: DNA
<213> ORGANISM: Artificial sequence
<220> FEATURE:
<223> OTHER INFORMATION: primer prm05458

<400> SEQUENCE: 7

```
ggggaccact ttgtacaaga aagctgggtc aaatgatcaa tagggtttta              50
```

<210> SEQ ID NO 8
<211> LENGTH: 57
<212> TYPE: DNA
<213> ORGANISM: Artificial sequence
<220> FEATURE:
<223> OTHER INFORMATION: primer prm06122

<400> SEQUENCE: 8

```
ggggacaagt ttgtacaaaa aagcaggctt aaacagtgag agaaaagaa agagaga      57
```

<210> SEQ ID NO 9
<211> LENGTH: 54
<212> TYPE: DNA
<213> ORGANISM: Artificial sequence
<220> FEATURE:
<223> OTHER INFORMATION: primer prm05447

<400> SEQUENCE: 9

```
ggggacaagt ttgtacaaaa aagcaggctt aaacaatggc tctcgtggag gata         54
```

-continued

<210> SEQ ID NO 10
<211> LENGTH: 48
<212> TYPE: DNA
<213> ORGANISM: Artificial sequence
<220> FEATURE:
<223> OTHER INFORMATION: primer prm05448

<400> SEQUENCE: 10
ggggaccact ttgtacaaga aagctgggtg atcatggagg tggagcag                48

<210> SEQ ID NO 11
<211> LENGTH: 64
<212> TYPE: DNA
<213> ORGANISM: Artificial sequence
<220> FEATURE:
<223> OTHER INFORMATION: primer prm06021

<400> SEQUENCE: 11
ggggacaagt ttgtacaaaa aagcaggctt aaacaatgac ttttacagag aaagatgaag    60
cttt                                                                 64

<210> SEQ ID NO 12
<211> LENGTH: 56
<212> TYPE: DNA
<213> ORGANISM: Artificial sequence
<220> FEATURE:
<223> OTHER INFORMATION: primer prm06022

<400> SEQUENCE: 12
ggggaccact ttgtacaaga aagctgggtc taagctacct attccttcat ctcagc        56

<210> SEQ ID NO 13
<211> LENGTH: 12
<212> TYPE: PRT
<213> ORGANISM: Artificial sequence
<220> FEATURE:
<223> OTHER INFORMATION: synthetic sequence

<400> SEQUENCE: 13

Glu Glu Thr Ala Arg Phe Gln Pro Gly Tyr Arg Ser
1               5                   10

<210> SEQ ID NO 14
<211> LENGTH: 10
<212> TYPE: PRT
<213> ORGANISM: Artificial sequence
<220> FEATURE:
<223> OTHER INFORMATION: synthetic sequence

<400> SEQUENCE: 14

Glu Gln Lys Leu Ile Ser Glu Glu Asp Leu
1               5                   10

<210> SEQ ID NO 15
<211> LENGTH: 7
<212> TYPE: PRT
<213> ORGANISM: Artificial sequence
<220> FEATURE:
<223> OTHER INFORMATION: synthetic sequence

<400> SEQUENCE: 15

Asp Tyr Lys Asp Asp Asp Lys
1               5

```
<210> SEQ ID NO 16
<211> LENGTH: 9
<212> TYPE: PRT
<213> ORGANISM: Artificial sequence
<220> FEATURE:
<223> OTHER INFORMATION: synthetic sequence

<400> SEQUENCE: 16

Tyr Pro Tyr Asp Val Pro Asp Tyr Ala
1               5

<210> SEQ ID NO 17
<211> LENGTH: 12
<212> TYPE: PRT
<213> ORGANISM: Artificial sequence
<220> FEATURE:
<223> OTHER INFORMATION: synthetic sequence

<400> SEQUENCE: 17

Glu Asp Gln Val Asp Pro Arg Leu Ile Asp Gly Lys
1               5                   10

<210> SEQ ID NO 18
<211> LENGTH: 11
<212> TYPE: PRT
<213> ORGANISM: Artificial sequence
<220> FEATURE:
<223> OTHER INFORMATION: synthetic sequence

<400> SEQUENCE: 18

Tyr Thr Asp Ile Glu Met Asn Arg Leu Gly Lys
1               5                   10

<210> SEQ ID NO 19
<211> LENGTH: 159
<212> TYPE: PRT
<213> ORGANISM: Gossypium hirsutum

<400> SEQUENCE: 19

Met Gly Phe Thr Glu Lys Gln Glu Gly Leu Val Lys Glu Ser Trp Glu
1               5                   10                  15

Val Leu Lys Gln Asp Ile Pro His Ser Ser Leu Arg Phe Phe Ser Leu
            20                  25                  30

Ile Leu Glu Ile Ala Pro Gly Ala Lys Asn Met Phe Ser Phe Leu Arg
        35                  40                  45

Glu Ser Glu Glu Ile Pro Gln Asn Asn Pro Lys Leu Lys Ala His Ala
    50                  55                  60

Val Lys Val Phe Lys Met Thr Cys Glu Ser Ala Ile Gln Leu Arg Glu
65                  70                  75                  80

Lys Gly Glu Val Val Val Ala Asp Thr Thr Leu Lys Tyr Leu Gly Thr
                85                  90                  95

Val His Val Lys Ser Gly Val Lys Asp Pro His Phe Glu Val Val Lys
            100                 105                 110

Glu Ala Leu Leu Arg Thr Ile Glu Glu Ala Ile Gly Glu Glu Lys Trp
        115                 120                 125

Asn Glu Glu Met Lys Asn Ala Trp Gly Glu Ala Tyr Asp Gln Leu Ala
    130                 135                 140

Glu Ala Ile Lys Ala Glu Met Lys Asn His His Asp Glu Thr Ala
145                 150                 155

<210> SEQ ID NO 20
<211> LENGTH: 156
```

```
<212> TYPE: PRT
<213> ORGANISM: Lycopersicon esculentum

<400> SEQUENCE: 20

Met Gly Phe Thr Asp Lys Gln Glu Ala Leu Val Arg Asp Ser Trp Glu
1               5                   10                  15

Phe Met Lys Gln Asp Ile Pro Gln Leu Ser Leu Arg Phe Phe Ser Leu
            20                  25                  30

Ile Leu Glu Ile Ala Pro Val Ala Lys Asn Met Phe Ser Phe Leu Lys
        35                  40                  45

Asp Ser Asp Glu Leu Pro Glu Asn Asn Pro Lys Leu Arg Ala His Ala
    50                  55                  60

Val Lys Val Phe Lys Met Thr Cys Glu Ser Ala Ile Gln Leu Arg Glu
65                  70                  75                  80

Lys Gly Glu Val Val Val Gly Glu Thr Thr Leu Lys Tyr Leu Gly Ser
                85                  90                  95

Ile His Leu Gln Lys Arg Val Ala Asp Pro His Phe Gly Val Val Lys
            100                 105                 110

Glu Ala Leu Leu Arg Thr Val Lys Glu Ala Thr Gly Asn Lys Trp Lys
        115                 120                 125

Asp Glu Met Lys Glu Ala Trp Ser Glu Ala Tyr Asp Gln Leu Ala Ser
    130                 135                 140

Ala Ile Lys Ala Glu Met His Ala Gly Ala Ala
145                 150                 155

<210> SEQ ID NO 21
<211> LENGTH: 152
<212> TYPE: PRT
<213> ORGANISM: Casuarina glauca

<400> SEQUENCE: 21

Met Ala Leu Thr Glu Lys Gln Glu Ala Leu Leu Lys Gln Ser Trp Glu
1               5                   10                  15

Val Leu Lys Gln Asn Ile Pro Ala His Ser Leu Arg Leu Phe Ala Leu
            20                  25                  30

Ile Leu Glu Ala Ala Pro Glu Ser Lys Tyr Val Phe Ser Phe Leu Lys
        35                  40                  45

Asp Ser Asn Glu Ile Pro Glu Asn Asn Pro Lys Leu Lys Ala His Ala
    50                  55                  60

Ala Val Ile Phe Lys Thr Ile Cys Glu Ser Ala Thr Glu Leu Arg Gln
65                  70                  75                  80

Lys Gly His Ala Val Trp Asp Asn Asn Thr Leu Lys Arg Leu Gly Ser
                85                  90                  95

Ile His Leu Lys Asn Lys Ile Thr Asp Pro His Phe Glu Val Met Lys
            100                 105                 110

Gly Ala Leu Leu Gly Thr Ile Lys Glu Ala Ile Lys Glu Asn Trp Ser
        115                 120                 125

Asp Glu Met Gly Cys Ala Trp Thr Glu Ala Tyr Asn Gln Leu Val Ala
    130                 135                 140

Thr Ile Lys Ala Glu Met Lys Glu
145                 150
```

METHOD FOR PRODUCING TRANSGENIC PLANTS WITH INCREASED YIELD, COMPRISING EXPRESSING OF HAEMOGLOBIN FROM *ARABIDOPSIS*

This application is the US national phase of international application PCT/EP2004/050405, filed 1 Apr. 2004, which designated the U.S. and claims priority of EP 03075974.0, filed 1 Apr. 2003, the entire contents of each of which are hereby incorporated by reference.

FIELD OF INVENTION

The present invention concerns a method for altering growth characteristics of plants, in particular a method for altering stress tolerance and yield in plants. More specifically, the present invention concerns altering tolerance in plants to various environmental stresses and to increasing seed yield by modifying plant haemoglobin gene expression and/or by modifying plant haemoglobin protein levels.

BACKGROUND

Most varieties of crop plants available to agriculture today have been obtained as a result of years of breeding activities focussed on the selection of higher yielding plants adapted to a particular environment. As a consequence, they often lack sufficient genetic variability to adapt to other environments whilst maintaining a high yield. In addition, during their life cycle, plants are exposed to various environmental conditions which greatly influence development and which, when unfavourable, may limit the final yield. Climate and other environmental conditions introduce variability into both total production and in quality of the product obtained over different seasons. Therefore it is a major aim in agriculture to develop varieties with enhanced stability in a quantitative and qualitative sense. Stability in production in the quantitative sense would be beneficial for planning and could avoid anomalies in production. In the qualitative sense, stability would contribute to improve post-harvest treatments and to industrial processing of agricultural products.

Yield is normally defined as the measurable produce of economic value from a crop. This may be defined in terms of quantity and/or quality. Yield is directly dependent on several factors, for example, the number and size of the organs, plant architecture (for example, the number of branches), seed production and more. Root development, nutrient uptake and stress tolerance are also important factors influencing yield.

The ability to influence one or more of the abovementioned factors, and to thereby increase crop yield, would have many applications in areas such as crop enhancement, plant breeding, production of ornamental plants, arboriculture, horticulture, forestry, production of algae or plants (for example for use as bioreactors, for the production of substances such as pharmaceuticals, antibodies, or vaccines, or for the bioconversion of organic waste or for use as fuel in the case of high-yielding algae and plants).

The final yield of a plant is determined by several parameters amongst which growth is a major contributor. Often an increase in growth correlates with higher yield. Particularly relevant is the capacity of a plant to maintain growth and to continue its developmental programme in unfavourable conditions. Unfavourable conditions are those that limit a plant in achieving its potential maximum production. Given the plant's inability of locomotion as a means of responding to environmental stimuli, plants are exposed to a variety of stresses that limit their performance. Abiotic stress conditions, such as shortage or excess of solar energy, water and nutrients, extremes of hot and cold temperatures, pollution (e.g. heavy-metal pollution) can all have a major impact on plant growth and can significantly reduce plant yield and growth.

The response of a plant to abiotic stresses, such as drought, temperature and osmotic stress, are intimately linked to each other (Zhu et al., Crit. Rev. Plant Sci. 16, 253-277, 1997). Many genes that are regulated by one type of stress are also responsive to the other two. A gene conferring tolerance to, for example, osmotic stress may therefore also confer tolerance to cold and drought stresses. In addition, a plant can be exposed to a multiplicity of stresses during its life cycle e.g. drought stress is often accompanied by high temperature stress. The most common kind of stress plants receive from their surroundings is temperature stress. Each plant species has its own optimal temperature for growth, and its geographical distribution is determined to a major extent by the temperature zone in which it can survive. Recently, concerns have been voiced about the potentially serious effects on agriculture of radical global temperature changes predicted to occur in the near future. There is now an effort to search for practical approaches to improve adaptability of plants to non-optimal temperature conditions. Molecular breeding methods have been applied to address these problems. For example, genetically engineered cold tolerance in plants has been achieved by overexpression of transcription factors such as SCOF-1 or CBF1 (Kim et al., Plant J. 25, 247-259, 2001; Jaglo-Ottosen et al., Science 280, 104-106, 1998); increasing the content of compatible solutes, (Alia et al., Plant Cell Environm. 21, 232-239, 1998); altering membrane lipids; and by reducing the effect of active oxygen species. The ability to withstand high temperatures has been obtained by engineering expression of heat shock proteins, increasing production of compatible solutes, and by altering membrane lipids. However to date there has been no scientific report describing the involvement of plant class-2 non-symbiotic haemoglobin genes in responses to environmental stresses or of plant haemoglobin genes in general in responses to temperature stresses.

Drought, salt stress and high or low temperature stress, are major problems in agriculture because these adverse environmental factors prevent crop plants from maximally exploiting their genetic potential. These stresses influence virtually every aspect of plant physiology and metabolism. Stress generally involves adaptive responses, such as morphological changes in roots or other organs, but also developmental changes, e.g. inhibition of growth. In general the response of a plant can be divided into three categories: maintenance of homeostasis, which includes ion homeostasis and osmotic homeostasis or osmotic adjustment; detoxification of harmful compounds, e.g. of reactive oxygen species or of damaged proteins that originated during the stress; and recovery of growth, that is, relief from growth inhibition and the effects on cell division and expansion imposed during the stress.

Progress has been made through genetic engineering in achieving stress tolerance by manipulating homeostasis, e.g. by increasing the concentrations of osmolytes (Nuccio et al., Curr. Opin. Plant Biol. 2, 128-34, 1999), by overexpressing Na+/H+ antiporters, (Apse and Blumwald, Curr. Opin. Biotechnol. 13, 146-50, 2002) or by overexpressing LEA proteins that may contribute to maintenance of membrane or protein stability (Xu et al., Plant Physiol. 110, 249-257, 1996). Engineering components of the osmotic signalling pathway is also a promising route to achieve osmotic stress tolerance. However, there is no report in the literature establishing a crucial role of haemoglobin genes in improving osmotic stress tolerance.

Haemoglobins are commonly found in a wide range of organisms (Vinogradov et al., Comp. Biochem. Physiol. 106, 1-26, 1993; Bolognesi et al., Prog. Biophys. Mol. Biol. 68, 29-68, 1997). With the possible exception of barley, all examined plant species have at least two haemoglobin genes. These genes have been reported to contain 3 conserved introns, a feature shared with animal haemoglobins (Arredondo-Peter et al., Plant Physiol. 118, 1121-1125, 1998). Based on their structure, plant haemoglobins used to be divided into two groups. The first is a group of symbiotic haemoglobins (leghaemoglobins), comprising haemoglobins that are abundantly present in infected cells of $N_2$-fixing nodules in leguminous plants but that can also be found in non-leguminous plants. The second group comprises non-symbiotic haemoglobins, which are ancestral to the symbiotic type of haemoglobins and which are more widespread in the plant kingdom.

In a more recent classification (Hunt et al., Plant Mol. Biol. 47, 677-692, 2001), haemoglobins were grouped into class 1 or class 2, depending on their amino acid sequence. Haemoglobins that did not fit into either class were assigned to a class 0 that was later renamed into class 3 (Wittenberg et al., J. Biol. Chem. 277: 871-874, 2002). Because the different classes are delineated based on primary amino acid sequences, symbiotic haemoglobins and non-symbiotic haemoglobins may be found in both class 1 or 2. Class 3 comprises the truncated haemoglobins. Members of these three classes not only differ in amino acid sequence, but also in biochemical properties. Truncated haemoglobins are small proteins carrying a haeme group that is able to bind oxygen. Class 1 and class 2 haemoglobins can be discriminated from each other in the conservation of certain amino acids in the sequence (see Hunt et al., 2001 for a detailed description of classes 1 and 2). Class 2 haemoglobins have conserved proline residues at positions B3 and G3, the absence of which may cause a different orientation in the B and G helices in class 1 haemoglobins. Additional substitutions and changes in charge at certain positions in the sequence cause further modifications in the packing of these helices.

The symbiotic haemoglobins are predominantly found in nodules of leguminous and in non-leguminous plants living symbiotically with bacteria. In plants, symbiotic haemoglobins are known to play a role in oxygen transport, thereby stimulating nitrogen fixation by providing oxygen to the nodules. This is made possible by the high affinity for oxygen that the leghaemoglobins have, combined with a fast dissociation constant for oxygen (Appleby, Sci. Prog. 76, 365-398, 1992). Leghaemoglobins belong to a multigene family and are usually posttranslationally modified. The bacterial haemoglobin from *Vitreoscilla* sp. resembles the leghaemoglobins in its binding properties for oxygen and because of this property the protein has been used to promote growth in plants and micro-organisms (U.S. Pat. No. 5,049,493; U.S. Pat. No. 5,959,187). *Vitreoscilla* haemoglobin has a $K_D$ of 6000 nM, whereas the *Arabidopsis* class-2 haemoglobin has a $K_D$ of 130 nM, which is more than 45 times lower. This high $K_D$ makes *Vitreoscilla* haemoglobin well suited for stimulating oxygen transport and consequently plant growth. Therefore, *Vitreoscilla* haemoglobin is quite distinct from plant non-symbiotic haemoglobins (Bülow et al., Trends Biotechnol. 17, 21-24, 1999). The use of *Vitreoscilla* haemoglobin may be compared to the use of bovine haemoglobin for promoting oxygen transfer in plant cell culture media and for plant regeneration (Azhakanandam et al., Enzyme Microb. Technol. 21, 572-577, 1997).

The non-symbiotic haemoglobins on the other hand differ from the leghaemoglobins in their primary protein structure (Arredondo-Peter et al., 1998). In addition, non-symbiotic plant haemoglobins have a very high affinity for oxygen, with a moderate association constant and a very low dissociation constant (about 40 times lower than the dissociation constant for oxygen of symbiotic haemoglobins (Arredondo-Peter et al., 1998; Bülow et al., 1999; Watts et al., Proc. Natl. Acad. Sci USA 98, 10119-10124)). Consequently oxygen is stably bound and a role in oxygen sensing or oxygen transport is not likely (Arredondo-Peter et al., 1998). However little is known about the functions in planta of the non-symbiotic haemoglobins. Their biochemical properties seem to exclude a role in oxygen diffusion, though a role as oxygenase may be possible (Hill, Can. J. Bot. 76, 707-712, 1998). The binding of oxygen causes a conformational change that may affect associated ligand molecules, thereby triggering certain physiological responses (Goodman and Hargrove, J. Biol. Chem. 276, 6834-6839, 2001).

Class 1 haemoglobins are induced by hypoxia, increasing sucrose concentrations (Trevaskis et al., Proc. Natl. Acad. Sci. USA 94, 12230-12234, 1997) or by nitrates (Wang et al., Plant Cell 12, 1491-1510, 2000). They are also expressed in germinating seeds and in roots of mature plants (Hunt et al., 2001) and in differentiating cells (Ross et al., Protoplasma 218, 125-133, 2001). Class 1 non-symbiotic haemoglobins are induced upon hypoxic stress (Hunt et al., 2001). *Arabidopsis* haemoglobin 1 enhances survival under hypoxic stress and promotes early shoot and root growth in *Arabidopsis thaliana* (Hunt et al., Proc. Natl. Acad. Sci. USA 99, 17197-17202, 2002). The use of class-1 haemoglobin molecules for altering plant growth characteristics was mainly focused towards manipulating oxygen levels in the plant. Tarczynski and Shen (U.S. Pat. No. 6,372,961) propose the use of maize haemoglobin to modify the oxygen concentrations in a plant cell and to stimulate seed germination and seedling growth of plants. Similarly, overexpression of haemoglobin from barley was shown to increase the ATP content in maize cells and to maintain the energy status under hypoxic stress (Guy et al., WO 00/00597).

The expression pattern of class-2 haemoglobins is different from that of class 1 haemoglobins in that they are expressed during embryogenesis and seed maturation, around openings (e.g. in mesophyl cells of stomata, around the top of the style, around the pore of the nectaries) or at branch points (e.g. to the bolt system, around emerging lateral roots, at the junction of anther and filament) (Hunt et al., 2001). Members of the class-2 haemoglobins are also responsive to cytokinin (Hunt et al., 2001). Harper et al. (WO 02/16655) have shown that haemoglobin 2 is induced in *Arabidopsis* upon cold, osmotic and saline stress, together with over 400 other genes. However, this class-2 haemoglobin has not been linked to increased stress tolerance. To date, only a few class-2 haemoglobin sequences have been described, among which is the GLB2 from *Arabidopsis thaliana* and two ESTs from *Beta vulgaris* that were isolated from stressed seedlings (GenBank acc no BE590299) and from a leaf cDNA library (GenBank acc no BQ586966).

DETAILED DESCRIPTION OF THE INVENTION

Surprisingly, the inventors have now demonstrated that plant class-2 non-symbiotic haemoglobins are useful for increasing the yield of a plant and for increasing abiotic stress. Therefore and according to a first embodiment of the present invention, there is provided a method for altering plant characteristics selected from one or more of increased yield, increased biomass, or altered cell division of a plant, comprising increasing expression in a plant of a nucleic acid sequence encoding plant class-2 non-symbiotic haemoglobin. Preferably, the increase in yield comprises increased seed yield.

The term "increased yield" or "increased biomass" encompasses an increase in biomass in one or more parts of a plant relative to the biomass of corresponding wild-type plants. The term also encompasses an increase in seed yield, which includes an increase in the biomass of the seed (which may be represented as weight of individual seeds or as total seed weight) and/or an increase in the number of (filled) seeds and/or in the size of the seeds and/or an increase in seed volume, each relative to corresponding wild-type plants. An increase in seed size and/or volume may also influence the composition of seeds. An increase in seed yield may be due to an increase in the number and/or size of flowers. An increase in yield may also increase the harvest index, which is expressed as a ratio of the total biomass over the yield of harvestable parts, such as seeds. The harvested part of a plant may differ from crop to crop, for example it may be seed (in the case of rice, sorghum or corn grown for seed); it may be above-ground biomass (in the case of corn, used as silage, or sugarcane), root (e.g. sugar beet), fruit (e.g. tomato), cotton fibres, or any other part of the plant which is of economic value. For example, the methods of the present invention may be used to increase the seed yield of rice and corn or to increase yield of silage corn in terms of overall above ground biomass and energy content. An increase in yield also encompasses a better performance of the plant under non-stress conditions or under stress conditions compared to wild-type plants. Stress conditions include any type of environmental stress and biotic and abiotic stresses.

The term "modified cell division" encompasses an increase or decrease in cell division or an abnormal cell division/cytokinesis, altered plane of division, altered cell polarity, altered cell differentiation. Modified cell division may also give rise to altered cell size and cell number. Modified cell division in a plant may furthermore result in modified growth of that plant.

The term "modified plant growth" as used herein encompasses, but is not limited to, a faster rate of growth in one or more parts of a plant (including seeds), at one or more stages in the life cycle of a plant (including germination), each relative to corresponding wild-type plants. Increased growth rate during the early stages in the life cycle of a plant may give rise to enhanced vigour, compared to corresponding wild-type plants. According to a preferred feature of the present invention, the faster growth rate takes place during substantially the majority of the plant's life cycle. An increase in growth rate may also alter the harvest time of a plant allowing plants to be harvested sooner than would otherwise be possible. If the growth rate is sufficiently increased, it may even give rise to the possibility of sowing further seeds of the same plant species (for example sowing and harvesting of rice plants followed by sowing and harvesting of further rice plants all within one conventional growing period) or of different plants species (for example the sowing and harvesting of rice plants followed by, for example, the sowing and optional harvesting of soy bean, potatoes or any other suitable plant), thereby increasing the annual biomass production per acre (due to an increase in the number of times (say in a year) that any particular plant may be grown and harvested).

According to another embodiment of this invention, there is provided a method for altering architecture of a plant, comprising increasing expression in a plant of a nucleic acid sequence encoding plant haemoglobin, preferably a non-symbiotic haemoglobin, more preferably a class-2 non-symbiotic haemoglobin.

"Altered architecture" may be due to a change in cell division. The term "architecture" as used herein encompasses the appearance or morphology of a plant, including any one or more structural features or a combination of structural features. Such structural features include the shape, size, number, position, texture, arrangement, and pattern of any cell, tissue or organ or groups of cells, tissues or organs of a plant, including the root, leaf, shoot stem, petiole, trichome, flower, inflorescence (for monocotyledonous and dicotyledonous plants), panicles, petal, stigma, style, stamen, pollen, ovule, seed, embryo, endosperm, seed coat, aleurone, fibre, cambium, wood, heartwood, parenchyma, aerenchyma, sieve element, phloem or vascular tissue, amongst others. Modified architecture therefore includes all aspects of modified growth of the plant. Sometimes plants modify their architecture in response to certain conditions such as stress and pathogens (e.g. nematodes). Therefore, within the scope of the term "architecture" is included modified architecture under stress conditions, whether biotic or abiotic stress conditions.

According to a further embodiment of the present invention, a method is provided for increasing stress tolerance of a plant, preferably abiotic stress tolerance, comprising increasing expression in a plant of a nucleic acid sequence encoding plant class-2 non-symbiotic haemoglobin.

"Increased stress tolerance" as used herein comprises, for any given stress, increasing tolerance in plants to that particular stress, whether those plants already have some degree of tolerance to the particular stress or whether that plant is being provided with tolerance to that stress anew. The altered stress tolerance is preferably altered tolerance to various abiotic stresses. Abiotic stresses are caused by elements present in the environment, which may include, but are not limited to: osmotic stress, drought, salt, dehydration, freezing, heat, cold, water logging, wounding, mechanical stress, oxidative stress, ozone, high light, heavy metals, nutrient deprivation, toxic chemicals and combinations of the same. Some of these stresses can also occur as a consequence of infection by pathogens (such as viruses, bacteria, fungi, insects or nematodes). According to a preferred feature of the present invention, increased abiotic stress tolerance is increased tolerance to osmotic stress.

In the case where abiotic stress is high temperature stress, any plant haemoglobin can be used for increasing stress tolerance. Therefore, there is provided a method for increasing high temperature stress tolerance of a plant, comprising increasing expression in a plant of a nucleic acid sequence encoding plant haemoglobin, preferably a non-symbiotic haemoglobin, more preferably a class-2 non-symbiotic haemoglobin.

The term "high temperature stress" refers to a stress condition caused by temperatures that are above the optimal growth temperature for a given plant. The term "increased tolerance" includes the capacity of a plant to endure any given stress to a greater degree than corresponding wild type plants. This may be manifested by, say, improved growth or survivability of the plant relative to corresponding wild type plants. The term also includes faster resumption of growth and/or development following a period of stress. It may also be that in certain applications it would be advantageous to decrease the tolerance in a plant to a particular type of stress. Altered stress tolerance therefore also includes decreasing tolerance in a plant to any given stress, i.e. making the plant more susceptible to any given stress. This may be advantageous for, for example, the production of certain metabolites.

Performance of the methods according to the present invention advantageously results in plants having altered growth characteristics, comprising increased yield and/or modified cell division and/or altered architecture and/or increased stress tolerance, in particular increased osmotic stress tolerance and/or high temperature stress tolerance.

According to preferred feature of the present invention, the haemoglobin useful in the methods according to the invention is a plant haemoglobin, preferably a non-symbiotic haemoglobin from a dicotyledonous plant. Further preferably the non-symbiotic haemoglobin which is derived from a dicotyledonous plant is a non-symbiotic class-2 haemoglobin. The classification of haemoglobins into class 1 or 2 is according to Hunt et al. (2001).

Advantageously, the methods according to the present invention for altering architecture or for increasing yield, biomass and/or cell division may be practised with a class-2 non-symbiotic haemoglobin from a dicotyledonous plant Preferably, the class-2 non-symbiotic haemoglobin originates from a member of the Brassicaceae, such as *Arabidopsis thaliana*, most preferably, the class-2 non-symbiotic haemoglobin is encoded by a sequence essentially similar to any one of SEQ ID NO 1, 3 or 5, or is a protein essentially similar to any one of SEQ ID NO 2, 4, 6, or is a homologous plant class-2 non-symbiotic haemoglobin with at least 65% sequence identity to SEQ ID NO 2.

Advantageously, where the plant characteristic to be altered is stress tolerance, the haemoglobin may be any class-2 non-symbiotic haemoglobin from a dicotyledonous plant, but preferably the class-2 non-symbiotic haemoglobin is isolated from the Brassicaceae, more preferably from *Beta vulgaris*, most preferably, the class-2 non-symbiotic class-2 haemoglobin is encoded by a nucleic acid sequence essentially similar to SEQ ID NO 1, or is a protein essentially similar to SEQ ID NO 2, or is a homologous plant class-2 non-symbiotic haemoglobin with at least 65% sequence identity to SEQ ID NO 2.

The sequences encoding the complete non-symbiotic haemoglobin from *Beta vulgaris* were hitherto unknown. Therefore according to another aspect of the present invention, there is provided an isolated nucleic acid sequence encoding a plant class-2 non-symbiotic haemoglobin selected from:

(i) a nucleic acid sequence comprising a sequence according to SEQ ID NO 1 or the complement thereof;

(ii) a nucleic acid sequence encoding a protein with an amino acid sequence which is at least, in increasing order of preference, 79%, 80%, 85%, 90%, 95%, 96%, 97%, 98% or 99% identical to the amino acid sequence as given in SEQ ID NO 2;

(iii) a nucleic acid encoding a protein comprising the amino acid sequence as given in SEQ ID NO 2;

(iv) a nucleic acid according to any of (i) to (iii) which is degenerate as a result of the genetic code;

(v) a nucleic acid which is a splice variant of a nucleic acid according to any of (i) to (iv);

(vi) a nucleic acid which is divergent due to differences between alleles encoding a protein as given in SEQ ID NO 2, or as defined in (i) to (v);

(vii) a nucleic acid encoding an immunologically active and/or functional fragment of a protein encoded by a DNA sequence according to any of (i) to (vi); and (viii) a nucleic acid sequence which hybridises, preferably under stringent conditions, to sequences defined in (i) to (vii), with the proviso that none of (i) to (viii) include the sequence as given in GenBank acc no BE590299 or BQ586966.

The nucleic acid sequence as set forth in SEQ ID NO 1 (also referred to as clone BvXero2), encodes a class-2 haemoglobin from *Beta vulgaris*. Advantageously, the methods according to the present invention may also be practised using nucleic acids (i) to (viii). These nucleic acids encompass nucleic acids encoding homologues, derivatives and functional fragments of the protein encoded by the sequence depicted in SEQ ID NO 1. The term also includes at least a part of SEQ ID NO 1; a complement of the sequence presented by SEQ ID NO 1; RNA, DNA, cDNA or genomic DNA corresponding to the sequence of SEQ ID NO 1; a variant of SEQ ID NO 1 due to the degeneracy of the genetic code; a family member of the gene or protein; an allelic variant of SEQ ID NO 1; different splice variants and variants of SEQ ID NO 1 that are interrupted by one or more intervening sequences.

The terms "gene(s)", "polynucleotide(s)", "nucleic acid sequence(s)", "nucleotide sequence(s)", "DNA sequence(s)" or "nucleic acid molecule(s)", as used herein refers to nucleotides, either ribonucleotides or deoxyribonucleotides or a combination of both, in a polymeric form of any length. These terms furthermore include double-stranded and single-stranded DNA and RNA. These terms also include known nucleotide modifications such as methylation, cyclisation and 'caps' and substitution of one or more of the naturally occurring nucleotides with an analogue such as inosine. The terms also encompass peptide nucleic acids (PNAs), a DNA analogue in which the backbone is a pseudopeptide consisting of N-(2-aminoethyl)-glycine units rather than a sugar. PNAs mimic the behaviour of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors. With "recombinant" DNA molecule is meant a hybrid DNA produced by joining pieces of DNA from different sources. With "heterologous" nucleotide sequence is intended a sequence that is not naturally occurring with the promoter sequence. While this nucleotide sequence is heterologous to the promoter sequence, it may be homologous, or native, or heterologous, or foreign, to the plant host.

A "coding sequence" or "open reading frame" or "ORF" is defined as a nucleotide sequence that can be transcribed into mRNA and/or translated into a polypeptide when placed under the control of appropriate regulatory sequences, i.e. when the coding sequence or ORF is present in an expressible format. The coding sequence or ORF is bound by a 5' translation start codon and a 3' translation stop codon. A coding sequence or ORF may include RNA, mRNA, cDNA, recombinant nucleotide sequences, synthetically manufactured nucleotide sequences or genomic DNA. The coding sequence or ORF may be interrupted by intervening nucleic add sequences.

Genes and coding sequences encoding substantially the same protein but isolated from different sources may consist of substantially divergent nucleic acid sequences. Reciprocally, substantially divergent nucleic add sequences may be designed to effect expression of essentially the same protein. These nucleic acid sequences are the result of e.g. the existence of different alleles of a given gene, or of the degeneracy of the genetic code or of differences in codon usage. Differences in preferred codon usage are illustrated in http://www.kazusa.or.jp/codon. Allelic variants are further defined as to comprise single nucleotide polymorphisms (SNPs) as well as small insertion/deletion polymorphisms (INDELs; the size of INDELs is usually less than 100 bp). SNPs and INDELs form the largest set of sequence variants in naturally occurring polymorphic strains of most organisms. Additionally or alternatively, in particular conventional breeding programs, such as for example marker assisted breeding, it is sometimes practical to introduce allelic variation in the plants by mutagenic treatment of a plant. One suitable mutagenic method is EMS mutagenesis. Identification of allelic variants then takes place by, for example, PCR. This is followed by a selection step for selection of superior allelic variants of the sequence in question and which give rise to altered growth characteristics. Selection is typically carried out by monitoring growth performance of plants containing different allelic variants of the sequence in question (for example, SEQ ID NO 1). Monitoring growth performance may be done in a greenhouse or in the field. Further optional steps include crossing plants, in which the superior allelic variant was identified, with another plant. This could be used, for example, to make a combination of interesting phenotypic features.

According to another aspect of the present invention, advantage may be taken of the nucleotide sequence capable of altering expression of a nucleic acid encoding haemoglobin in breeding programs. For example, in such a program, a DNA marker is identified which may be genetically linked to a gene capable of altering the activity of haemoglobin in a plant (which gene may be a gene encoding a haemoglobin or another gene capable of influencing the activity of a haemoglobin). This DNA marker is then used in breeding programs to select plants having altered growth characteristics. Many techniques are nowadays available to identify SNPs and/or INDELs.

"Hybridisation" is a process wherein substantially homologous complementary nucleotide sequences anneal to each other. The hybridisation process may occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process may also occur with one of the complementary nucleic acids immobilised to a matrix such as magnetic beads, Sepharose beads or any other resin. Tools in molecular biology relying on such a process include the isolation of poly (A+) mRNA. The hybridisation process may furthermore occur with one of the complementary nucleic acids immobilised to a solid support such as a nitrocellulose or nylon membrane or immobilised by e.g. photolithography to e.g. a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. High stringency conditions for hybridisation include high temperature and/or low salt concentration (salts include NaCl and $Na_3$-citrate) and/or the inclusion of formamide in the hybridisation buffer and/or lowering the concentration of compounds such as Sodium Dodecyl Sulphate (SDS) in the hybridisation buffer and/or exclusion of compounds such as dextran sulphate or polyethylene glycol (promoting molecular crowding) from the hybridisation buffer. Conventional hybridisation conditions are described e.g. (Sambrook et al. 2001) but the skilled craftsman will appreciate that numerous different hybridisation conditions may be designed in function of the known or expected homology and/or length of the nucleic acid sequence. Sufficiently low stringency hybridisation conditions are particularly preferred to isolate nucleic adds heterologous to the DNA sequences of the invention defined supra. Elements contributing to the heterology include allelism, degeneration of the genetic code and differences in preferred codon usage as discussed supra.

The invention also relates to DNA sequences hybridising under stringent conditions to the DNA sequences according to the invention with the proviso that the hybridising DNA sequence as given in GenBank acc no BE590299 or BQ586966 is excluded.

DNA sequences may also be interrupted by intervening sequences. With "intervening sequences" is meant any nucleic acid sequence which disrupts a coding sequence comprising the DNA sequence according to the invention or which disrupts the expressible format of a DNA sequence comprising the DNA sequence according to the invention. Removal of the intervening sequence restores the coding sequence or the expressible format. Examples of intervening sequences include introns, mobilisable DNA sequences such as transposons and DNA tags such as a T-DNA. With "mobilisable DNA sequence" is meant any DNA sequence that may be mobilised as a result of a recombination event.

The term "fragment of a sequence" means a truncated version of the sequence in question. The truncated sequence (nucleic acid or protein sequence) may vary widely in length while the maximum size is not critical. Typically, the truncated amino acid will range from about 5 to about 60 amino acids in length. In case of a "functional fragment", the minimum size is a sequence of sufficient size to provide this sequence with at least a comparable function and/or activity to the original sequence which was truncated, The functionality of haemoglobin may be determined for example by spectroscopy or by kinetic analysis of $O_2$ binding (Arredondo-Peter et al., 1997).

"Immunologically active" refers to molecules or specific fragments thereof, such as specific epitopes or haptens, that are recognised by (i.e. that bind to) antibodies. Specific epitopes may be determined using, for example, peptide-scanning techniques as described in Geysen et al., Chem Biol., 3 (8), 679-88, 1996. Functional fragments may also include those comprising an epitope which is specific for the proteins according to the invention.

The present invention also provides an isolated plant class-2 non-symbiotic haemoglobin protein comprising one of the polypeptides selected from:
   a a polypeptide as represented by SEQ ID NO 2;
   b a polypeptide with an amino acid sequence which is at least, in increasing order of preference, 79%, 80%, 85%, 90%, 95% 96%, 97%, 98% and 99% identical to the amino acid sequence as given in SEQ ID NO: 2;
   c a polypeptide encoded by a nucleic acid sequence as defined above;
   d a homologue, derivative, immunologically active and/or functional fragment of a protein as defined in any of (i) to (iii).

Advantageously, proteins according to any of a to d above may be used in the methods of the present invention. Proteins essentially similar to the protein according to the invention comprise at least a part of SEQ ID NO 2, functional fragments, homologues, derivatives, substitutional variants, deletional variants and insertional variants of SEQ ID NO 2, as well as the protein presented in SEQ ID NO 2 itself.

The terms "protein(s)", "peptide(s)", "polypeptide(s)" or "oligopeptide(s)", when used herein refer to amino acids in a polymeric form of any length. These terms also include known amino acid modifications such as disulphide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamines, deoxyhexoses, hexoses, sialic acid etc.), acylation and radio-labelling (e.g. with $^{125}I$, $^{131}I$, $^{35}S$, $^{14}C$, $^{32}P$, $^{33}P$, $^{3}H$) as well as non-naturally occurring amino acid residues, L-amino acid residues and D-amino acid residues.

"Homologues" of a protein of the invention are those peptides, oligopeptides, polypeptides, proteins and enzymes which contain amino acid substitutions, deletions and/or additions relative to a protein with respect to which they are a homologue, without altering one or more of its functional properties, in particular without reducing the activity of the resulting product. For example, a homologue of a protein will consist of a bioactive amino acid sequence variant of the protein. To produce such homologues, amino acids present in the protein may be replaced with other amino acids having similar properties, for example hydrophobicity, hydrophilicity, hydrophobic moment, antigenicity, propensity to form or break alpha-helical structures or beta-sheet structures, and so on.

Substitutional variants of a protein of the invention are those in which at least one residue in the protein amino acid sequence has been removed and a different residue inserted in its place. Amino acid substitutions are typically of single residues, but may be clustered depending upon functional constraints placed upon the polypeptide; insertions will usually be of the order of about 1-10 amino acid residues and deletions will range from about 1-20 residues. Preferably, amino acid substitutions will comprise conservative amino acid substitutions.

Insertional amino acid sequence variants of a protein of the invention are those in which one or more amino acid residues are introduced into a predetermined site in a protein. Insertions may comprise amino-terminal and/or carboxy-terminal fusions as well as intra-sequence insertions of single or multiple amino acids. Generally, insertions within the amino acid sequence will be smaller than amino or carboxyl terminal fusions, for example of the order of about 1 to 10 residues. Examples of amino- or carboxy-terminal fusion proteins or peptides include the binding domain or activation domain of a transcriptional activator as used in the yeast two-hybrid system, phage coat proteins, (histidine)$_6$-tag, glutathione S-transferase, protein A, maltose-binding protein, dihydrofolate reductase, Tag•100 epitope (EETARFQPGYRS (SEQ ID NO:13)), c-myc epitope (EQKLISEEDL (SEQ ID NO:14)), FLAG-epitope (DYKDDDK (SEQ ID NO:15)), lacZ, CMP (calmodulin-binding peptide), HA epitope (YPYDVPDYA (SEQ ID NO:16)), protein C epitope (EDQVDPRLIDGK (SEQ ID NO:17)) and VSV epitope (YTDIEMNRLGK (SEQ ID NO:18)).

Deletional variants of a protein of the invention are characterised by the removal of one or more amino acids from the amino acid sequence of the protein.

Amino acid variants of a protein of the invention may readily be made using peptide synthetic techniques well known in the art, such as solid phase peptide synthesis and the like, or by recombinant DNA manipulations. The manipulation of DNA sequences to produce variant proteins, which are manifested as substitutional, insertional or deletional variants are also well known in the art. For example, techniques for making substitution mutations at predetermined sites in DNA having a known sequence are well known to those skilled in the art, such as by M13 mutagenesis, T7-Gen in vitro mutagenesis kit (USB, Cleveland, Ohio), QuickChange Site Directed mutagenesis kit (Stratagene, San Diego, Calif.), PCR-mediated site-directed mutagenesis or other site-directed mutagenesis protocols. Another alternative to manipulate DNA sequences to produce variant proteins, which are manifested as substitutional, insertional or deletional variants, comprises targeted in vivo gene modification which may be achieved by chimeric RNA/DNA oligonucleotides as described by e.g. (Palmgren, Trends Genetics 13 (9), 348, 1997; Yoon et al., Proc. Natl. Acad. Sci U.S.A., 93 (5), 2071-2076, 1996).

"Derivatives" of a protein of the invention are those peptides, oligopeptides, polypeptides, proteins and enzymes which comprise at least about five contiguous amino acid residues of the polypeptide but which retain the biological activity of the protein. A "derivative" may further comprise additional naturally-occurring, altered glycosylated, acylated or non-naturally occurring amino acid residues compared to the amino acid sequence of a naturally-occurring form of the polypeptide. Alternatively or in addition, a derivative may comprise one or more non-amino add substituents compared to the amino acid sequence of a naturally occurring form of the polypeptide, for example a reporter molecule or other ligand, covalently or non-covalently bound to the amino acid sequence such as, for example, a reporter molecule which is bound thereto to facilitate its detection.

Methods for the search and identification of homologues of the haemoglobin are known to a person skilled in the art. Methods for the alignment of sequences for comparison are also well known in the art, such methods include GAP, BEST-FIT, BLAST, FASTA and TFASTA. The BLAST algorithm calculates percent sequence identity and performs a statistical analysis of the similarity between the two sequences. The software for performing BLAST analysis is publicly available through the National Centre for Biotechnology information. GAP uses the algorithm of Needleman and Wunsch (J. Mol. Biol. 48: 443-453, 1970) to find the alignment of two complete sequences that maximises the number of matches and minimises the number of gaps. When using the Needleman-Wunsch algorithm for determining the percentage identity between two protein sequences, the full length sequences are preferably used in combination with the BLOSUM62 matrix, a gap opening penalty of 10 or 11 and a gap extension penalty of 0.5 or 1.

The cDNA insert of the plasmid pYPGEXERO2 present in clone BvXero2 contains an 860 bp cDNA (SEQ ID NO 1, named BvXERO2) with an open reading frame of 456 base pairs encoding a polypeptide of 152 amino acids (SEQ ID NO 2) with a predicted molecular weight of 16.72 kD. This polypeptide, named Xero2, comprises the amino acid residues that are conserved for all plant haemoglobins. These include the cd1 phenylalanine, C2 proline and F8 proximal histidine residues needed for haeme binding and the E7 distal histidine which is involved in ligand binding in many classes of haemoglobin. This nomenclature is in accordance with the three dimensional structure naming system used for animal haemoglobins (Dickerson and Geis, Hemoglobin: Structure, function, Evolution and Pathology, Benjamin-Cummings, Menlo Park, USA), wherein helices are designated by an upper-case letter and interhelical domains are designated by two lower-case letters. The number refers to the position along the domain starting at the N-terminal end. BvXero2 falls in the group GLB2, described for non-symbiotic plant haemoglobins. This group contains the conserved residues His (E7), His (F8) and Phe (cd11) (Hunt et al., 2001 and Trevaskis et al., 1997). Expression analysis of the ARAth GLB2 promoter show that expression is localised in roots, leaves and inflorescence and may be induced in young plants by cytokinin treatment, but is not induced by abscisic acid, 2,4-dichlorophenoxyacetic acid, giberellic acid, benzo (1,2, 3) thiadiazole-7-carbothioic acid S-methyl ester or methyl jasmonate (Hunt et at, 2001).

This polypeptide may be produced by introducing into a host cell an isolated nucleic acid molecule or a nucleic acid construct according to the invention as described below, culturing the host cell under conditions allowing expression of the polypeptide and recovering the produced polypeptide from the culture.

Further advantageously, the methods of the present invention are applicable to organisms other than plants, for example the invention is applicable to yeast and bacteria. The ability to provide yeast with tolerance to various stresses may have many economic advantages relevant to the baking industry, the brewing industry and others. Tolerance to heat and osmotic stresses are of particular economic advantage. Similarly, the ability to provide bacteria with tolerance to various stresses may also be advantageous. For example, bacteria or yeasts with enhanced tolerance to osmotic and heat stress may be particularly suited for large-scale fermentation processes, as they allow the use of more concentrated nutritive media and are better adapted against the heat produced by the metabolic processes in such fermentation. The present invention thus also provides a host cell comprising a nucleic acid sequence or nucleic acid construct as described above, wherein the host cell is a bacterial, yeast, fungal, plant or animal cell. The isolated polypeptide may also be produced by chemical synthesis.

Advantageously, altering expression of a nucleic acid sequence encoding a haemoglobin and/or altering of activity of the haemoglobin itself may be effected by chemical means, i.e. by exogenous application of one or more compounds or elements capable of altering activity of the haemoglobin and/or capable of altering expression of a haemoglobin gene (which may be either an endogenous gene or a transgene introduced into a plant). The exogenous application may comprise contacting or administering cells, tissues, organs or organisms with the gene product or a homologue, derivative or active fragment thereof and/or to antibodies to the gene product. Such antibodies may comprise "plantibodies", single chain antibodies, IgG antibodies and heavy chain camel antibodies, as well as fragments thereof. Altering expression of a nucleic acid sequence encoding a haemoglobin and/or altering of activity of the haemoglobin itself may also be effected as a result of decreased levels of factors that directly or indirectly activate or inactivate a haemoglobin. Additionally or alternatively, contacting or administering cells, tissues, organs or organisms with an interacting protein or to an inhibitor or activator of the gene product provides another exogenous means for altering expression of a nucleic acid sequence encoding a haemoglobin (which may be endogenous or be present as a transgene) and/or for altering activity of the haemoglobin encoded by this nucleic acid sequence.

Therefore, according to one aspect of the present invention, there is provided a method for modifying the growth characteristics of a plant, comprising exogenous application of one or more compounds or elements capable of altering expression of a haemoglobin gene and/or capable of altering activity of a haemoglobin protein.

Additionally or alternatively, and according to a preferred embodiment of the present invention, altering expression of a nucleic acid sequence encoding a haemoglobin and/or altering activity of the haemoglobin itself may be effected by recombinant means. Such recombinant means may comprise a direct and/or indirect approach for altering of expression of a nucleic acid sequence and/or for altering of the activity of a protein.

For example, an indirect approach may comprise introducing, into a plant, a nucleic acid sequence capable of altering activity of the protein in question (a haemoglobin) and/or expression of the gene in question (a gene encoding a haemoglobin). The haemoglobin gene or the haemoglobin protein may be wild type, i.e. the native or endogenous nucleic acid or polypeptide. Alternatively, it may be a nucleic acid derived from the same or another species, which gene is introduced as a transgene, for example by transformation. This transgene may be substantially modified from its native form in composition and/or genomic environment through deliberate human manipulation. Also encompassed by an indirect approach for altering activity of an haemoglobin and/or expression of a haemoglobin gene is the inhibition or stimulation of regulatory sequences that drive expression of the native gene or transgene. Such regulatory sequences may be introduced into a plant.

A direct and preferred approach on the other hand comprises introducing into a plant a nucleic add sequence encoding a haemoglobin or a homologue, derivative or active fragment thereof. The nucleic acid sequence may be introduced into a plant by, for example, transformation. The nucleic acid sequence may be derived (either directly or indirectly (if subsequently modified)) from any source provided that the sequence, when expressed in a plant, leads to altered expression of a haemoglobin nucleic acid/gene or altered activity of a haemoglobin protein. The nucleic acid sequence may be isolated from a microbial source, such as bacteria, yeast or fungi, or from a plant, algal or animal (including human) source. This nucleic acid may be substantially modified from its native form in composition and/or genomic environment through deliberate human manipulation. The nucleic acid sequence is preferably a homologous nucleic acid sequence, i.e. a nucleic acid sequence obtained from a plant, whether from the same plant species or different.

Another embodiment of the present invention provides a nucleic acid construct comprising a nucleic acid sequence according to the invention, as described above. The nucleic add construct may be an expression vector, wherein the nucleic acid sequence is operably linked to one or more control sequences allowing expression of the sequence in prokaryotic and/or eukaryotic host cells.

Thus, according to the present invention, there is provided a nucleic acid construct, comprising:
  (i) an isolated nucleic acid sequence according to any of (i) to (viii) as defined above; and
  (ii) one or more control sequences controlling expression of the nucleic acid sequence of (i); and optionally,
  (iii) a transcription terminator sequence.

Preferably, the isolated nucleic acid sequence (i) of the nucleic acid construct above is as represented by SEQ ID NO 1. To effect expression of a protein in a cell, tissue or organ, preferably of plant origin, either the protein may be introduced directly to a cell, such as by microinjection or ballistic means or alternatively, an isolated nucleic acid molecule encoding the protein may be introduced into a cell, tissue or organ in an expressible format. Preferably, the DNA sequence of the invention comprises a coding sequence or open reading frame (ORF) encoding the polypeptide of the invention or a homologue or derivative thereof or an immunologically active fragment thereof as defined supra.

With "vector" or "vector sequence" is meant a DNA sequence, which may be introduced in an organism by transformation and which may be stably maintained in that organism. Vector maintenance is possible in e.g. cultures of *Escherichia coli, Agrobacterium tumefaciens, Saccharomyces cerevisiae* or *Schizosaccharomyces pombe*. Other vectors such as phagemids and cosmid vectors may be maintained and multiplied in bacteria and/or viruses. Vector sequences generally comprise a set of unique sites recognised by restriction enzymes, the multiple cloning site (MCS), in which one or more inserts may be inserted. With "insert" is meant a DNA sequence which is integrated in one or more of the sites of the MCS comprised within a vector. "Expression vectors" form a subset of vectors which comprise regulatory sequences enabling expression of the protein encoded by (an) insert(s). Expression vectors are known in the art enabling protein expression in organisms including bacteria (e.g. *E. coli*), fungi (e.g. *S. cerevisiae, S. pombe, P. pastoris*), insect cells (e.g. baculoviral expression vectors), animal cells (e.g. COS or CHO cells) and plant cells (e.g. potato virus X-based expression vectors, see e.g. Vance et al. 1998—WO 98/44097). The invention includes any vector or expression vector comprising an insert encoding a protein according to the invention, homologues, derivatives, functional and/or immunologically active fragments thereof as defined supra.

By "expressible format" is meant that the isolated nucleic add molecule is in a form suitable for being transcribed into mRNA and/or translated to produce a protein, ether constitutively or following induction by an intracellular or extracellular signal, such as an environmental stimulus or stress (mitogens, anoxia, hypoxia, temperature, salt, light, dehydration, etc.) or a chemical compound such as IPTG (isopropyl-β-D-thiogalactopyranoside) or such as an antibiotic (tetracycline, ampicillin, rifampicin, kanamycin), hormone (e.g. gibberellin, auxin, cytokinin, glucocorticoid, brassinosteroid, ethylene, abscisic acid etc), hormone analogue (iodoacetic acid (IAA), 2,4-D, etc), metal (zinc, copper, iron, etc), or dexamethasone, amongst others. As will be known to those skilled in the art, expression of a functional protein may also require one or more post-translational modifications, such as glycosylation, phosphorylation, dephosphorylation, or one or more protein-protein interactions, amongst others. All such processes are included within the scope of the term "expressible format".

"Expression" means the production of a protein or nucleotide sequence in the cell itself or in a cell-free system. It includes transcription into an RNA product, post-transcriptional modification and/or translation to a protein product or polypeptide from a DNA encoding that product, as well as possible post-translational modifications. Preferably, expression of a protein in a specific cell, tissue, or organ, preferably of plant origin, is effected by introducing and expressing an isolated nucleic add molecule encoding the protein, such as a cDNA molecule, genomic gene, synthetic oligonucleotide molecule, mRNA molecule or open reading frame, to the cell, tissue or organ, wherein the nucleic add molecule is placed in operable connection with suitable regulatory sequences including a promoter, preferably a plant-expressible promoter, and optionally a terminator sequence.

"Regulatory sequence" refers to control DNA sequences, which are necessary to affect the expression of coding sequences to which they are ligated and the stability of the transcription products resulting from these coding sequences. The nature of such control sequences differs depending upon the host organism. In prokaryotes, control sequences generally include promoters, ribosomal binding sites, and terminators. In eukaryotes, control sequences generally include promoters, terminators and enhancers or silencers. The term "control sequence" is intended to include, as a minimum, all components necessary for expression and may also include additional advantageous components which determine when, how much and where a specific gene is expressed, as well as influence the stability of transcripts. Reference herein to a "promoter" is to be taken in its broadest context and includes the transcriptional regulatory sequences derived from a classical eukaryotic genomic gene, including the TATA box which is required for accurate transcription initiation, with or without a CCAAT box sequence and additional regulatory elements (i.e. upstream activating sequences, enhancers and silencers) which after gene expression in response to developmental and/or external stimuli, or in a tissue-specific manner.

As used herein, the term "derived from" or "originated from" shall be taken to indicate that a particular integer or group of integers originates from the species specified but has not necessarily been obtained directly from the specified source.

Regulatory sequences herein also refer to any of the group comprising a promoter, enhancer, silencer, intron sequence, 3'UTR and/or 5'UTR region, protein and/or RNA stabilizing elements. The term "promoter" also includes the transcriptional regulatory sequences of a classical prokaryotic gene, in which case it may include a −35 box sequence and/or a −10 box transcriptional regulatory sequences. The term "promoter" is also used to describe a synthetic or fusion molecule or derivative, which confers, activates or enhances expression of a nucleic add molecule in a cell, tissue or organ. Promoters may contain additional copies of one or more specific regulatory elements, to further enhance expression and/or to alter the spatial expression and/or temporal expression of a nucleic acid molecule to which it is operably connected. Such regulatory elements may be placed adjacent to a heterologous promoter sequence to drive expression of a nucleic acid molecule in response to external stimuli or to confer expression of a nucleic acid molecule to specific cells, tissues or organs such as meristems, leaves, roots, embryo, flowers, seeds or fruits.

In the context of the present invention, the promoter is preferably a plant-expressible promoter sequence. Promoters, however, that also function or solely function in non-plant cells such as bacteria, yeast cells, insect cells and animal cells are not excluded from the invention, for example where the methods of the invention are applied in modifying stress tolerance of yeast. By "plant-expressible" is meant that the promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. In the present context, a "regulated promoter" or "regulatable promoter sequence" is a promoter that is capable of conferring expression on a structural gene in a particular cell, tissue or organ, or group of cells, tissues or organs of a plant, optionally under specific conditions, however, it generally does not confer expression throughout the plant under all conditions. Accordingly, a regulatable promoter sequence may be a promoter sequence that drives expression of a gene to which it is operably connected in a particular location within the plant or alternatively throughout the plant under a specific set of conditions, such as following induction of gene expression by a chemical compound or other elicitor.

A regulatable promoter that may be used in the performance of the present invention confers expression in a specific location within the plant and/or a specific developmental phase of a plant, either constitutively or following induction. Included within the scope of such promoters are cell-specific promoter sequences, tissue-specific promoter sequences, organ-specific promoter sequences, cell cycle specific gene promoter sequences, inducible promoter sequences and constitutive promoter sequences that have been modified to confer expression in a particular part of the plant at any one time, such as by integration of a constitutive promoter within a transposable genetic element (Ac, Ds, Spm, En, or other transposon). Those skilled in the art will be aware that an "inducible promoter" is a promoter, the transcriptional activity of which is increased or induced in response to a developmental, chemical, environmental, or physical stimulus. Similarly, the skilled craftsman will understand that a "constitutive promoter" is a promoter that is transcriptionally active throughout most, but not necessarily all phases of growth and development of an organism, preferably a plant. In contrast, the term "ubiquitous promoter" is taken to indicate a promoter that is transcriptionally active throughout most, but not necessarily all parts of an organism, preferably a plant.

The term "cell-specific" shall be taken to indicate that expression is predominantly in a particular cell or cell-type, preferably of plant origin, albeit not necessarily exclusively in that cell or cell-type. Similarly, the term "tissue-specific" shall be taken to indicate that expression is predominantly in a particular tissue or tissue-type, preferably of plant origin, albeit not necessarily exclusively in that tissue or tissue-type. Similarly, the term "organ-specific" shall be taken to indicate that expression is predominantly in a particular organ, preferably of plant origin, albeit not necessarily exclusively in that organ.

Constitutive promoters or promoters that induce expression throughout the entire plant may be modified by the addition of nucleotide sequences derived from one or more tissue-specific promoters or tissue-specific inducible promoters, to confer tissue-specificity thereon. For example, the CaMV 35S promoter may be modified by the addition of maize Adh1 promoter sequence, to confer anaerobically-regulated root-specific expression thereon (Ellis et al., 1987). Another example includes conferring root specific or root abundant gene expression by fusing the CaMV35S promoter to elements of the maize glycine-rich protein GRP3 gene (Feix and Wulff 2000—WO0015662). Those skilled in the art will readily be capable of selecting appropriate promoter sequences from publicly-available or readily-available sources, for use in regulating expression of the polypeptides described supra.

A preferred promoter according to the invention would be a constitutive promoter such as GOS2 or CaMV 35S, or a promoter inducible by environmental stimuli, or a seed specific promoter.

Placing a nucleic acid molecule under the regulatory control of a promoter sequence, or in operable connection with a promoter sequence means positioning the nucleic acid molecule such that expression is controlled by the promoter sequence. A promoter is usually, but not necessarily, positioned upstream, or at the 5'-end, and within 2 kb of the start site of transcription of the nucleic acid molecule which it regulates. In the construction of heterologous promoter/structural gene combinations it is generally preferred to position the promoter at a distance from the gene transcription start site that is approximately the same as the distance between that promoter and the gene it controls in its natural setting (i.e., the gene from which the promoter is derived). As is known in the art, some variation in this distance may be accommodated without loss of promoter function. Similarly, the preferred positioning of a regulatory sequence element with respect to a heterologous gene to be placed under its control is defined by the positioning of the element in its natural setting (i.e., the gene from which it is derived). Again, as is known in the art, some variation in this distance may also occur.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. Where the control sequence is a promoter, it would be obvious for a skilled person to use a double-stranded nucleic acid.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants.

Examples of terminators particularly suitable for use in the gene constructs of the present invention include the *Agrobacterium tumefaciens* nopaline synthase (NOS) gene terminator, the *Agrobacterium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3'Bt2), the *Zea mays* zein gene terminator sequence, the rbcs-1A gene terminator, and the rbcs-3A gene terminator sequences, amongst others.

The nucleic acid constructs of the invention may further include an origin of replication sequence which is required for maintenance and/or replication in a specific cell type, for example a bacterial cell, when said nucleic acid construct is required to be maintained as an episomal genetic element (e.g. plasmid or cosmid molecule) in a cell. Preferred origins of replication include, but are not limited to, the f1-ori and colE1 origins of replication.

The nucleic acid construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of the invention or a derivative thereof. Suitable markers may be selected from markers that confer antibiotic or herbicide resistance. Cells containing the recombinant DNA will thus be able to survive in the presence of antibiotic or herbicide concentrations that kill untransformed cells. Examples of selectable marker genes include the bar gene which provides resistance to the herbicide Basta; the nptII gene which confers resistance to the antibiotic kanamycin and neomycin; the ampicillin resistance (Amp'), tetracycline resistance gene (Tc'), the hpt gene which confers hygromycin resistance, the phosphinothricin resistance gene, chloramphenicol acetyltransferase (CAT) gene, the hygromycin resistance gene. Visual markers, such as the Green Fluorescent Protein (GFP), β-glucuronidase (GUS) gene, and luciferase gene, amongst others may also be used as selectable markers.

Recombinant DNA constructs for use in the methods according to the present invention may be constructed using recombinant DNA technology well known to persons skilled in the art. The gene constructs may be inserted into vectors, which may be commercially, suitable for transforming into host cells, preferably plant cells, and suitable for expression of the gene of interest in the transformed cells.

According to a preferred feature of the present invention, the nucleic acid sequence encoding haemoglobin is overexpressed in a plant. Methods for obtaining enhanced or increased expression of genes or gene products are well documented in the art and include, for example, overexpression driven by a strong promoter, the use of transcription enhancers or translation enhancers.

On the other hand, downregulation of the nucleic acid sequence may also give rise to altered growth characteristics in a plant. Plants having modified growth characteristics may be obtained by expressing a nucleic acid sequence encoding haemoglobin in either sense or antisense orientation. Techniques for downregulation are well known in the art. "Gene silencing" or "downregulation" of expression, as used herein, refers to lowering levels of gene expression and/or levels of active gene product and/or levels of gene product activity. Such decreases in expression may be accomplished by, for example, the addition of coding sequences or parts thereof in a sense orientation (if it is desired to achieve co-suppression).

Nucleic acid constructs (genetic constructs) aimed at silencing gene expression may comprise the nucleotide sequence encoding a haemoglobin, for example the sequence itself as represented by SEQ ID NO 1 (or one or more parts thereof) in a sense and/or antisense orientation relative to the promoter sequence. The sense or antisense copies of at least part of the endogenous gene in the form of direct or inverted repeats may be utilized in the methods according to the invention. The characteristics of plants may also be altered by introducing into a plant at least part of an antisense version of the nucleotide sequence represented by SEQ ID NO 1. It should be clear that part of the nucleic acid could achieve the desired result.

Homologous anti-sense genes are preferred to heterologous anti-sense genes, homologous genes being plant genes, preferably plant genes from the same plant species, and heterologous genes being genes from non-plant species.

Another method for downregulation of gene expression or gene silencing comprises use of ribozymes, for example as described in Atkins et al. 1994 (WO 94/00012), Lenee et al. 1995 (WO 95/03404), Lutziger et al. 2000 (WO 00/00619), Prinsen et al. 1997 (WO 97/3865) and Scott et al. 1997 (WO 97/38116).

Gene silencing may also be achieved by insertion mutagenesis (for example, T-DNA insertion or transposon insertion), or by gene silencing strategies, including RNA mediated silencing, as described by, among others, Angell and Baulcombe 1998 (WO 98/36083), Lowe et al. 1989 (WO 98/53083), Lederer et al. 1999 (WO 99/15682) or Wang et al. 1999 (WO 99/53050). Expression of an endogenous gene essentially similar to SEQ ID NO 1, 3, or 5, or the activity of the encoded protein may also be reduced if there is a mutation on the endogenous gene.

Furthermore, the present invention also relates to a method for the production of a transgenic plant having altered growth characteristics when compared to wild type plants, comprising the steps of:

(i) introducing into a plant or plant cell a nucleic acid sequence encoding a haemoglobin according to the present invention; and (ii) cultivating this plant or plant cell under conditions promoting regeneration and/or mature plant growth.

The term "plant cell" comprises any cell derived from any plant and existing in culture as a single cell, a group of cells or a callus. A plant cell may also be any cell in a developing or mature plant in culture or growing in nature.

Advantageously, the methods of the invention are applicable to any plant. "Plant" or "Plants" comprise all plant species which belong to the superfamily Viridiplantae. The present invention is applicable to any plant, in particular monocotyledonous plants and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incarnate*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Omithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuge menziesii*, *Pterolobium stellatum*, *Pyrus communis*, *Quercus* spp., *Rhaphiolepis umbellate*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys verticillate*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylia*, *Vaccinium* spp., *Vicia* spp. *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash, and tea, amongst others, or the seeds of any plant specifically named above or a tissue, cell or organ culture of any of the above species. According to a preferred feature of the present invention, the plant is a crop plant comprising soybean, sunflower, canola, alfalfa, rapeseed or cotton. Further preferably, the plant according to the present invention is a monocotyledonous plant including members of the Poaceae, such as sugarcane, most preferably the plant is a cereal, such as rice, maize, wheat, millet, barley and sorghum, oats.

The present invention clearly extends to any plant cell or plant obtainable by any of the methods described herein, and to all plant parts and propagules thereof. The invention comprises any plant cell, plant part or plant having altered characteristics as described above, including increased yield, increased biomass, increased cell division, increased tolerance to osmotic stress and/or altered architecture, said plant cell, plant part or plant having increased expression of a nucleic acid sequence encoding a plant class-2 non-symbiotic haemoglobin and/or having altered activity of a plant class-2 non-symbiotic haemoglobin protein. The invention also comprises any plant cell, plant part or plant having increased tolerance to high temperature stress said plant cell, plant part or plant having increased expression of a nucleic acid sequence encoding a plant haemoglobin protein. Also transgenic harvestable parts or propagules of such plants are encompassed by the present invention, wherein the harvestable parts are selected from the group consisting of seeds, leaves, flowers, fruits, stem cultures, rhizomes, tubers and bulbs. The term plant furthermore encompasses suspension cultures, embryos, meristematic regions, callus tissue, leaves, seeds, roots, shoots, gametophytes, sporophytes, pollen, and microspores.

The present invention extends further to encompass the transgenic ancestors or progeny of a transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention.

The nucleic acid molecule or a nucleic acid construct comprising it may be introduced into a cell using any known method for the transfection or transformation of a cell. A whole organism may be regenerated from a single transformed or transfected cell, using methods known in the art. Plant tissue capable of subsequent clonal propagation, whether by organogenesis or embryogenesis, may be transformed with a nucleic acid construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The gene of interest is preferably introduced into a plant by transformation. The term "transformation" as referred to herein encompasses the transfer of an exogenous polynucleotide into a host cell, irrespective of the method used for transfer. The polynucleotide may be transiently or stably introduced into a host cell and may be maintained non-integrated, for example, as a plasmid, or alternatively, may be integrated into the host genome. The resulting transformed plant cell may then be used to regenerate a transformed plant in a manner known to persons skilled in the art. Transformation of a plant species is now a fairly routine technique.

Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. A preferred method according to the present invention is *Agrobacterium*-mediated transformation (An et al., EMBO J., 4, 277-284, 1985; Dodds, Plant genetic engineering, 1985; Herrera-Estrella et al., EMBO J., 2, 987-995, 1983; Herrera-Estrella et al., Nature, 303, 209-213, 1983), including the 'flower dip' transformation method; (Bechtold and Pelletier, Methods Mol. Biol., 82, 259-266, 1998; Trieu et al., Plant J., 22 (6), 531-541, 2000).

A whole plant may be regenerated from the transformed or transfected cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The term "organogenesis", as used herein, means a process by which shoots and roots are developed sequentially from meristematic centers. The term "embryogenesis", as used herein, means a process by which shoots and roots develop together in a concerted fashion (not sequentially), whether from somatic cells or gametes.

Generally after transformation, plant cells or cell groupings are selected for the presence of one or more markers which are encoded by plant-expressible genes co-transferred with the gene of interest, following which the transformed material is regenerated into a whole plant. Putatively transformed plants may be evaluated, for instance using Southern analysis, for the presence of the gene of interest, copy number and/or genomic organisation. Alternatively or additionally, expression levels of the newly introduced DNA may be undertaken using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention also relates to the use of a plant non-symbiotic haemoglobin or of a nucleic acid sequence encoding a plant non-symbiotic haemoglobin for altering characteristics of a plant.

In particular, the present invention relates to the use of a nucleic acid sequence encoding plant class-2 non-symbiotic haemoglobin for increasing one or more of yield, biomass or cell division of a plant. Preferably, the increased yield comprises at least increased seed yield.

The present invention furthermore relates to the use of a nucleic acid sequence encoding plant class-2 non-symbiotic haemoglobin for altering architecture of a plant.

Preferably, the nucleic acid sequence encoding plant class-2 non-symbiotic haemoglobin used for increasing one or more of yield, biomass or cell division of a plant or for altering architecture of a plant is isolated from a dicotyledonous plant, preferably from Brassicaceae, more preferably from *Arabidopsis thaliana*, most preferably the isolated nucleic acid is as represented by SEQ ID NO 3.

The present invention also relates to the use of a nucleic acid sequence encoding plant class-2 non-symbiotic haemoglobin for increasing abiotic stress tolerance of a plant. Preferably the abiotic stress is osmotic stress. The present invention also relates to the use of a nucleic acid sequence encoding plant haemoglobin for increasing high temperature tolerance of a plant, preferably said plant haemoglobin is a non-symbiotic haemoglobin, more preferably a class-2 non-symbiotic haemoglobin.

Preferably, the nucleic acid sequence encoding plant class-2 non-symbiotic haemoglobin for increasing osmotic stress tolerance or for increasing high temperature stress tolerance is isolated from a dicotyledonous plant, preferably from the Brassicaceae, more preferably from *Beta vulgaris*, most preferably the isolated nucleic acid is essentially similar to SEQ ID NO 1.

Furthermore, the present invention also relates to the use of a nucleic acid sequence encoding a haemoglobin and to the use of a haemoglobin itself for altering stress tolerance of bacteria or yeast. The invention further also extends to the use of a nucleic acid sequence encoding haemoglobin according to the present invention and homologues, derivatives and active fragments thereof and to the use of the haemoglobin itself and of homologues, derivatives and active fragments thereof in therapeutic or diagnostic compositions. The invention also extends to the use of a nucleic acid sequence encoding plant class-2 non-symbiotic haemoglobin according to the invention and homologues, derivatives and active fragments thereof and to the use of the haemoglobin itself and of homologues, derivatives and active fragments thereof in modulating levels of $O_2$ or other compounds, such as, for example, NO. In this respect, modulating levels of a plant class-2 non-symbiotic haemoglobin according to the invention may also be used to modify existing signal transduction pathways in organisms. Therefore the present invention also provides the use of a nucleic acid sequence encoding a plant class-2 non-symbiotic haemoglobin according to the invention and/or of the haemoglobin itself in modifying signal transduction pathways. These uses are also encompassed by the present invention.

The nucleic acid sequences hereinbefore described (and portions of the same and sequences capable of hybridising with the same) and the amino acid sequences hereinbefore described (and homologues, derivatives and active fragments of the same) are useful in modifying the growth characteristics of plants, as hereinbefore described. The sequences would therefore find use as growth regulators, such as herbicides or growth stimulators. The present invention also provides a composition comprising a protein represented by any of the aforementioned amino acid sequences or homologues, derivatives or active fragments thereof for use as a growth regulator.

DESCRIPTION OF FIGURES

FIG. 10: Sequence listing.

EXAMPLES

Figure 1:
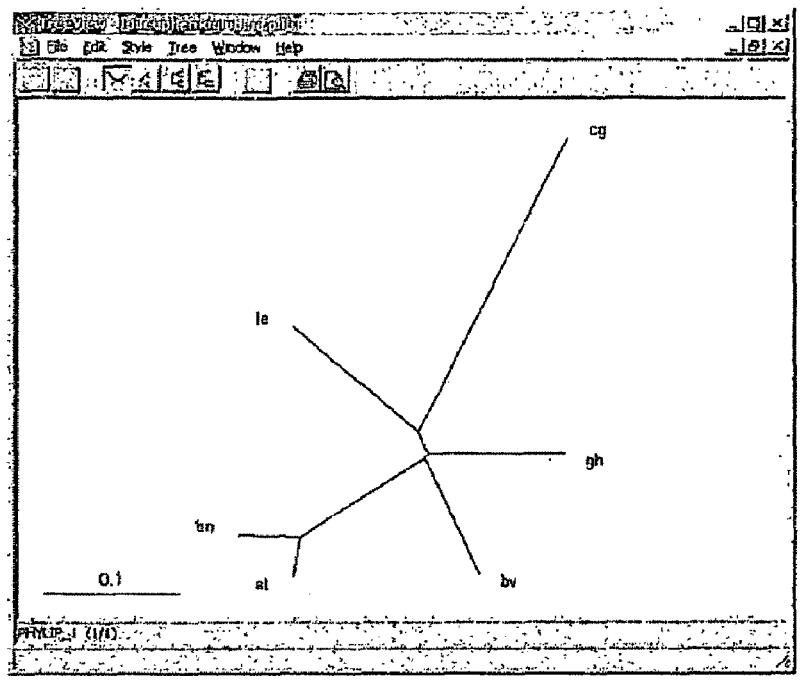
FIG. 1: Pileup and unrooted dendrogram showing homology between haemoglobin sequences from *Arabidopsis thaliana* (at, SEQ ID NO:4), *Brassica napus* (bn, SEQ ID NO:6), *Beta vulgaris* (bv, SEQ ID NO:2), *Gossypium hirsutum* (gh, SEQ ID NO:19), *Lycopersicon esculentum* (le, SEQ ID NO:20), *Casuarina glauca* (cg, SEQ ID NO:21).

The present invention will now be described with reference to the following examples, which are by way of illustration alone.

Unless stated otherwise in the Examples, all recombinant DNA techniques are performed according to protocols as described in Sambrook et al. (1989) or in Volumes 1 and 2 of Ausubel et al. (2000). Standard materials and methods for plant molecular work are described in R. D. D. Croy (1993).

Example 1

Construction of a Sugar Beet cDNA Library Induced by Salt Stress

Sugar beet seeds (*Beta vulgaris* cv. Dita) were sown on pots containing a mixture of sand and vermiculite (1:1 w/w). The plants were grown under greenhouse conditions (8 h at 20° C., 16 h at 25° C. with supplementary lighting to simulate a minimum 12 h photoperiod). The plants were periodically irrigated with a nutrient solution containing 2.4 g/l $Ca(NO_3)_2$. $4H_2O$, 1 g/l $KNO_3$, 1 g/l $MgSO_4.7H_2O$, 0.3 g/l $KH_2PO_4$, 5.6 mg/l Fequelate (Kelantren, Bayer), 1.1 mg/l $ZnSO_4.7H_2O$, 3.3 mg/l $MnO_4.H_2O$, 0.3 mg/l $CuSO_4.5H_2O$, 3.8 mg/l $H_3BO_3$, 0.18 mg/l $(NH_4)_6Mo_7.4H_2O$. For the construction of the cDNA library, 3-week old plants were irrigated with 200 mM NaCl the day preceding the harvesting.

Directional cDNA synthesis was performed with the cDNA Synthesis Kit (Stratagene) using poly(A)$^+$ RNA prepared from leaves of salt-treated sugar beet plants. The cDNA was ligated into the phage λPG15 vector and packed using Gigapack III Gold Packaging Extract (Stratagene). This phage carries the excisable expression plasmid pYPGE15 (URA3 as a selection marker) that may be used directly for both *E. coli* and yeast complementation (Brunelli and Pall, Yeast, 9, 1309-1318, 1993). A plasmid cDNA library was recovered from λPG15 with the cre-lox recombinase system (Brunelli and Pall, Yeast, 9, 1309-1318, 1993).

Example 2

Set-Up of a Screening Assay for Osmotic Stress Tolerance

The yeast strains used were the diploid strain W303/W303 (can1-100,his 3-11,15,leu2-3,112, trp1-1,ura3-1,GAL+) and a diploid mutant thereof, deficient for glycerol phosphate dehydrogenase (gpd1), named JM164, constructed from two haploid gpd1 mutant strains (YRA111(W303-1A gpd1:: TRP1 mat a) and YRA114 (W303-1A gpd1::TRP1 mat α)). The diploid strains were used because these prevent the isolation of recessive chromosomal mutations which might give tolerance to osmotic stress. The strains were grown on YPD medium (2% glucose, 2% peptone and 1% yeast extract) or on SD medium (2% glucose, 0.7% yeast nitrogen base (Difco) without amino acids, 50 mM MES [2-(N-morpholino)ethanesulfonic acid] adjusted to pH 5.5 with Tris (Tris(hydroximethyl) aminomethane), and the required amino acids, purine and pyrimidine bases).

In a first step, the sensitivity to sorbitol of a gpd1 mutant strain (JM164) was compared with that of a wild type diploid strain, in both YPD and SD medium. To this end, the yeast strains were grown on YPD or on SD medium with different concentrations of sorbitol, ranging from 1.3 M to 1.8 M at a temperature of 28° C. for 4 days. At 1.7 M sorbitol, a clear difference in growth was observed between the gpd1 mutant and the wild type. The gpd1 mutant strain was more sensitive compared to the wild type.

In a second step, the best conditions for the transformation were determined, optimising the amount of cells and the amount of library plasmid to be used in a transformation reaction. 300 ml of YPD was inoculated with 30 μl of a saturated preculture of JM164 cells. This culture was grown overnight until an $OD_{660}$≅0.8 was obtained. The yeast cells were centrifuged at 2000 rpm, washed with water and then washed with AcLiTE solution (0.1 M lithium acetate, 10 mM Tris-HCl pH 7.6 and 1 mM EDTA (Ethylene diamine tetraacetic acid, disodium salt)). The pellet of cells was resuspended in 2 ml of AcLiTE solution and incubated for 15 minutes with shaking at 300° C. After incubation, 200 μl of ssDNA (10 mg/ml) was added. The solution was then divided into 110 μl aliquots which were placed in an Eppendorf tube, and 200 ng of cDNA library were added. This was followed by heat shock transformation using the method described by Gietz et al in brief, 500 μl of PEG-AcLiTE solution (AcLiTE solution with 40% w/w of PEG (Polyethylene glycol) 4000) was added to each aliquot. After shaking, aliquots were incubated for 30 minutes at 300° C. and for twenty minutes at 42° C. The cells were then harvested and resuspended in 200 μl of 1M sorbitol. Two aliquots were plated onto 14 cm Ø Petri dishes containing SD with all the necessary supplements except tryptophan (marker for the gpd1 mutation), and uracil (marker for the plasmid). To quantify the efficiency of the transformation, four 55 μl aliquots were separated from the original cell pellet and inoculated with 0, 10, 50 and 100 ng of cDNA library. The same transformation protocol was then applied, and, at the end the cells were resuspended in 100 μl of sorbitol and plated onto a 7 cm Ø Petri dish containing the same SD solution. The average transformation efficiency for the JM164 strain was about 20 transformants for each ng of cDNA library.

Example 3

Isolation of Xero Genes

Three days after transformation, colonies had developed. The colonies were harvested in sterile water and the number of cells was quantified by plating different dilutions. The cell suspension obtained after harvesting was concentrated about ton times and was plated on YPD medium or SD medium containing 1.7 M sorbitol. The plates were incubated at 28° C. and colonies able to grow after four days were selected. The tolerance of the colonies isolated in the first round was rechecked on selective medium and those clones not giving significant tolerance were discarded. From the colonies that remained, the plasmid was eliminated by selection in minimal medium. This was done by obtaining stationary phase cultures of each strain in liquid YPD medium. These cultures were plated in YPD medium and after two days colonies were picked and replicated both in YPD and in SD without uracil and tryptophan; those able to grow in YPD, but unable to grow in SD-URA-TRP were selected and their tolerance was compared with the original, plasmid containing strain. As a final confirmation, the plasmid was recovered from the colonies able to pass the previous controls, transformed into the JM164 strain and again selected for those clones giving tolerance. The results obtained are summarised in Table 1:

TABLE 1

| Drought stress | Number of colonies on YPD | Number of colonies on SD |
|---|---|---|
| Number of transformants | ≅241000 | ≅241000 |
| Transformants isolated in 1$^{st}$ round | 55 | 40 |
| Clones with irreproducible tolerance | 11 | 2 |
| Tolerance independent of the plasmid | 37 | 36 |

TABLE 1-continued

| Drought stress | Number of colonies on YPD | Number of colonies on SD |
|---|---|---|
| Positive clones confirmed by retransformation | 7 | 2 |

The reconfirmed positive clones were sequenced, they encoded three different genes, named Xero1 to Xero3. Xero2 encoded a class-2 haemoglobin. A sequence alignment with other plant class-2 haemoglobins is given in FIG. 1.

Example 4

Xero2 Gives Tolerance to Osmotic Stress, but Also to High Temperature Stress in Yeast A dilution series of JM164 pYPGEXero2 and JM164 pYPGE (control) was plated on YPD medium with 1.7 M sorbitol and tested for osmotic tolerance after 2 and 4 days.

Figure 2:
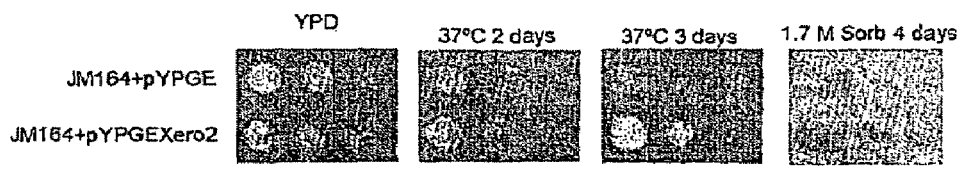
FIG. 2: The BvXero2 gene confers tolerance to both osmotic stress and high temperature in yeast. The upper row represents the wild-type yeast, the bottom row is the yeast strain transformed with BvXero2. From left to right: control on YPD, growth at 37° C. after 2 and 3 days, and growth on 1.7 M sorbitol after 4 days.

The yeast done with Xero2 had a strong sorbitol tolerance phenotype and the phenotype was very reproducible: at a concentration of 1.7 M sorbitol, control yeast cells did not grow at all, whilst yeast cells overexpressing Xero2 did (FIG. 2).

The definition of a strong phenotype is based on drop test experiments. Several dilutions of saturated cultures (1:10, 1:100, 1:1000) were made and these were grown on selective media (YPD with 1.7M sorbitol). "Strong phenotypes" were those clones that grew well in all the dilutions assayed. With "no strong phenotypes" is meant that the clone does not grow in all dilutions. The control cells expressing the empty plasmid did not grow at all in the selective media.

In the same way, JM164 pYPGEXERO2 and JM164 pYPGE were plated on YPD medium and incubated at 37° C. for 2 and 3 days. The JM164 pYPGEXERO2 clone showed a higher tolerance for elevated temperatures than the wild type (FIG. 2).

Tolerance to other toxic compounds such as lithium, sodium, hydrogen peroxide, menadione, and tert-Butyl Hydroperoxide (tBOOH) was also assayed but without any significative result.

Example 5

Southern Blotting Reveals More than One Isoform in Sugar Beet

Figure 3:
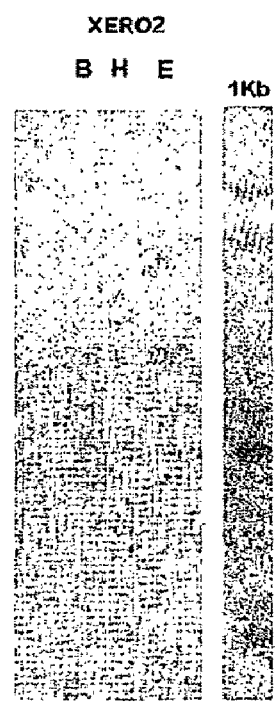
FIG. 3: Southern blot with BvXero2 as probe on genomic sugar beet DNA. Enzymes used were BamHI, HindIII and EcoRI. At the right 1 kb markers are depicted.

In order to confirm the presence of BvXero2 in the sugar beet genome and to estimate the number of genes encoding haemoglobin in this plant species, a Southern blot analysis was performed. Genomic DNA was prepared from leaves of 3-week old sugar beet leaves (Rogers S O and Bendich A J, Extraction of total cellular DNA from plants, algae and fungi (Eds) Plant molecular biology manual, Kluwer Academic Publishers, Dordrecht, Netherlands, 1994). 5 µg of DNA was digested with EcoRI, HindIII or BamHI, electrophoresed in 0.8% agarose gel and blotted onto a nylon membrane filter (Hybond N+, Amersham Life Science). The membrane filter was hybridised with a $^{32}$P-labelled probe corresponding to the 878 bp EcoRI-XhoI digestion fragment of pYPGEhemo, which spans the whole cDNA Hybridisation and washes were carried out under high stringency conditions (650° C.) (Church G M and Gilbert W., PNAS USA 81: 1991-1995 1984). The presence of several hybridisation fragments in all lanes, independent of the restriction endonucleases used to digest the genomic DNA, suggested that there are at least two isoforms of BvXero2 in sugar beet that hybridise with the whole cDNA (FIG. 3). The 878 bp probe may furthermore be used to detect and isolate other isoforms of BvXero2.

Example 6

BvXero2 is Induced by NaCl and ABA in Sugar Beet

In order to confirm that BvXero2 participates in the response of sugar beet plants to salt stress, the accumulation of BvXero2 mRNA in response to various exposure times to NaCl was analysed using northern blot analysis. Total RNA was isolated from control, 250 mM $Na^+$ or 100 µM ABA-treated sugar beet leaves as described by Davis et al. (Basic methods in Molecular Biology. Elsevier. Amsterdam pp. 143-146 1986). 30 µg of total RNA was separated on a 1% agarose gel containing 2.2% formaldehyde and blotted onto a nylon membrane filter (Hybond N, Amersham Life Science). Hybridization was performed using the above described probe.

Figure 4:
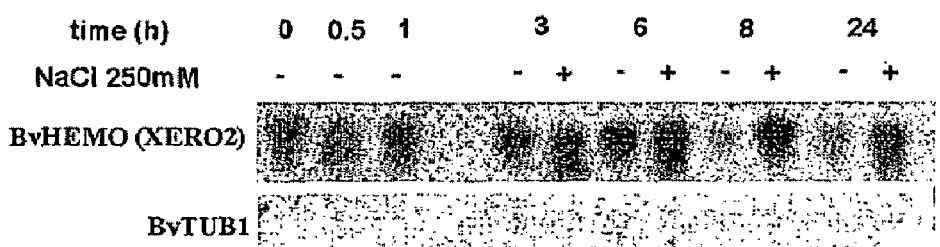
FIG. 4: Northern blot with BvXero2 as probe. Different time points (in hrs) after treating the sugar beet plants with 250 mM NaCl. $\alpha_3$-tubulin was used as control.
Figure 5:
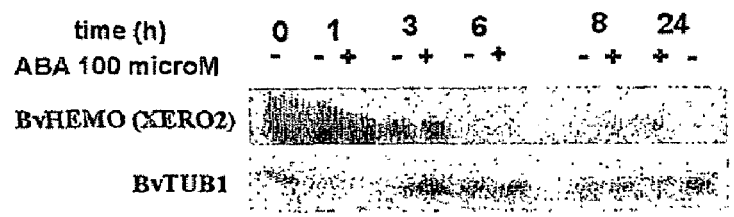
FIG. 5: Northern blot with BvXero2 as probe. Different time points (in hrs) after treating the sugar beet plants with 100 µM ABA $\alpha_3$-tubulin was used as control.

The BvXero2 specific probe showed only one band that corresponded to the size of the BvXero2 cDNA (0.45 kb). The filter was washed twice with 4×SSC buffer (0.6 M NaCl, 0.06 M trisodium citrate adjusted to pH=7 with HCl) 0.1% SDS for 5 minutes and twice with 0.4×SSC, 0.1SDS for five minutes at 65° C. The same filter was re-hybridised with a 1.9 EcoRI fragment comprising the $\alpha_3$-tubulin gene of *Arabidopsis thaliana* (Ludwig et al. Characterization of the α-tubulin gene family of *Arabidopsis thaliana* PNAS USA 84: 5833-5837 1987). As shown in FIG. 4 the BvXero2 mRNA accumulated with time upon NaCl treatment, and reached a maximum at 8 hours. The increase was about 10 fold as compared to control plants. This high level was maintained at least until 24 hrs after induction on NaCl. It is interesting to note that the sugar beet cDNA library used to search for genes involved in stress tolerance was also obtained from plants treated for 24 hours with NaCl. An induction of BvXero2 after 3 hours of ABA treatment was also observed (FIG. 5). This increase was observed even with a huge variation of the background level, which could be due to timing, or light induction. The increase was about 2 fold at three hours, but after six hours BvXERO2 almost disappeared in the control lanes, whilst the ABA treated lanes still showed a significant signal.

Example 7

*Arabidopsis thaliana* Transformed with AtHb2 (CDS2591)

Cloning of CDS2591

Figure 6:
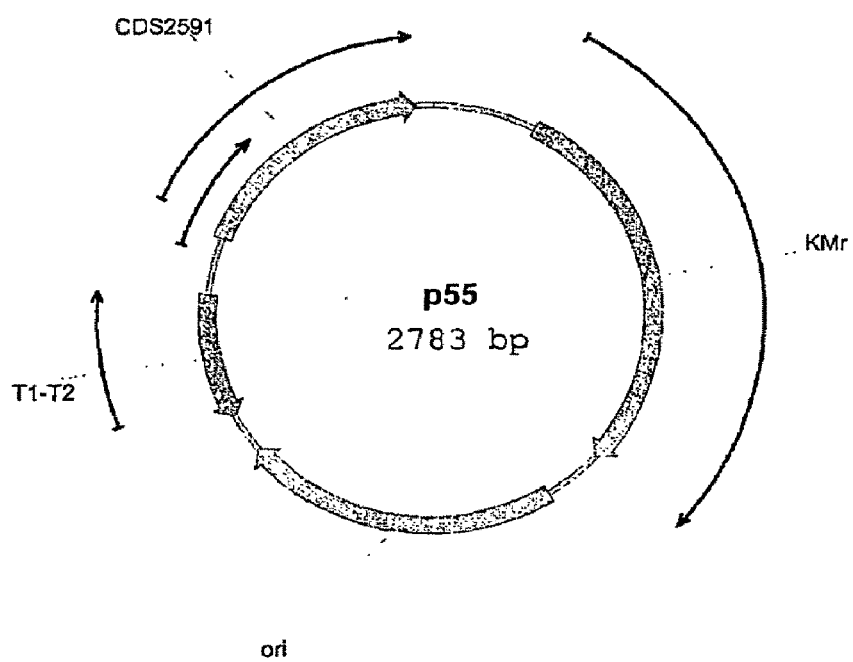
FIG. 6: Schematic representation of the entry done p55, containing CDS2591 within the AttL1 and AttL2 sites for Gateway® cloning in the pDONR201 backbone. CDS2591 is the internal code for the *Arabidopsis* non-symbiotic haemoglobin Hb2. This vector contains also a bacterial kanamycin-resistance cassette and a bacterial origin of replication.

The nucleic acid CDS2591 was amplified by PCR using an *Arabidopsis thaliana* seedling cDNA library (Invitrogen, Paisley, UK) as template. After reverse transcription of RNA extracted from seedlings, the cDNAs were cloned into pCMV Sport 6.0. Average insert size of the bank was 1.5 kb, and original number of clones was of 1.59×10$^7$ cfu. The original titer was determined to be 9.6×10$^5$ cfu/ml, after a first amplification it became 6×10$^{11}$ cfu/ml. After plasmid extraction, 200 ng of template was used in a 50 µl PCR mix. Primers prm6122 (SEQ ID NO 14) and prm5458 (SEQ ID NO 15), which include the AttB sites for Gateway recombination, were used for PCR amplification. PCR was performed using Hifi Taq DNA polymerase in standard conditions. A PCR fragment of 503 bp was amplified and purified, also using standard methods. The first step of the Gateway procedure, the BP reaction, was then performed, during which the PCR fragment recombined in viva with the pDONR plasmid to produce, according to the Gateway terminology, an "entry clone", p55 (FIG. 6). Plasmid pDONR201 was purchased from Invitrogen, as part of the Gateway® technology.

Vector Construction for Transformation with p35 S-CDS2591 Cassette

The entry clone p56 was subsequently used in an LR reaction with p1978, a destination vector used for *Arabidopsis* transformation. This vector contains as functional elements within the T-DNA borders: a plant selectable marker; a GFP expression cassette; and a Gateway cassette intended for LR in viva recombination with the sequence of interest already cloned in the entry clone. The p35 S promoter for constitutive expression is located upstream of this Gateway cassette.

Figure 7:
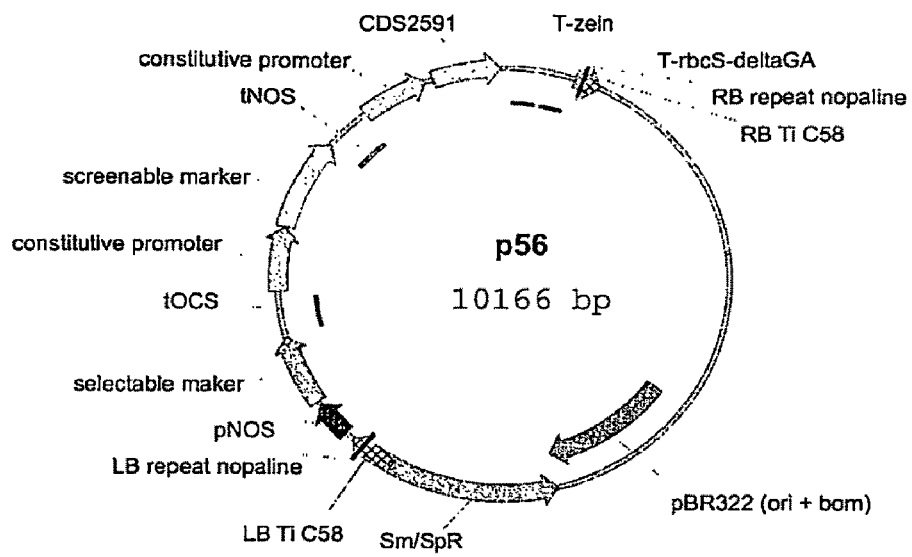
FIG. 7: Binary vector for the expression in plants of CDS2591 under the control of P35 S and the T-zein-T-rbcS-deltaGA double terminator sequence. CDS2195 is the internal code for *Arabidopsis* non-symbiotic haemoglobin Hb2. This vector contains a T-DNA derived from the Ti Plasmid, limited by a left border (LB repeat, LB Ti C58) and a right border (RB repeat, RB Ti C58)). From the left border to the right border, this T-DNA contains: a selectable marker cassette for antibiotic selection of transformed plants; a screenable marker cassette for visual screening of transformed plants; the 'constitutive promoter—CDS2591—zein and rbcS-deltaGA double terminator'. This vector also contains an origin of replication from pBR322 for bacterial replication and a selectable marker (Spe/SmeR) for bacterial selection with spectinomycin and streptomycin.

After the LR recombination step, the resulting expression vector p56 (FIG. 7) can be transformed into *Agrobacterium* strain C58C1RIF PMP90 and subsequently to *Arabidopsis* plants.

Transformation of *Arabidopsis* with p35 S-CDS2591

Sowing and Growing of the Parental Plants

For the parental plants, approximately 12 mg of wild-type *Arabidopsis thaliana* (ecotype Columbia) seeds was suspended in 27.5 ml of 0.2% agar solution. The seeds were incubated for 2 to 3 days at a temperature of 4° C. and then sown. The plants were germinated under the following standard conditions: 22° C. during the day, 18° C. at night, 65-70% relative humidity, 12 hours of photoperiod, sub-irrigation with water for 15 min every 2 or 3 days. The seedlings that developed were then transplanted to pots with a diameter of 5.5 cm, containing a mixture of sand and peat in a ratio of 1 to 3. The plants were then further grown under the same standard conditions as mentioned above.

*Agrobacterium* Growth Conditions and Preparation

*Agrobacterium* strain C58C1RIF with helper plasmid pMP90 containing vector p56 was inoculated in a 50 ml plastic tube containing 1 ml LB (Luria Broth) without antibiotic. The culture was shaken for 8-9 h at 28° C. Hereafter, 10 ml of LB without antibiotic was added to the plastic tube and shaken overnight at 28° C. At an optical density ($OD_{600}$) of approximately 2.0, 40 ml of 10% sucrose and 0.05% Silwet L-77 (a mixture of polyalkyleneoxide modified heptamethyltrisiloxane (84%) and allyloxypolyethyleneglycol methyl ether (16%), OSI Specialties Inc) was added to the culture. The *Agrobacterium* culture so obtained was labeled CD7659 and used to transform the grown plants.

Flower Dip

When each parental plant had one inflorescence of 7-10 cm in height, the inflorescences were inverted into the *Agrobacterium* culture and agitated gently for 2-3 seconds. 2 plants per transformation were used. The plants were then returned to the normal growing conditions as described above.

Seed Collection 5 weeks after the flowers were dipped in the *Agrobacterium* culture, watering of the plants was stopped. The plants were incubated at 25° C. with a photoperiod of 20 hours. One week later, the seeds were harvested and placed in a seed drier for one week. The seeds were then cleaned and collected in 15 ml plastic tubes. The seeds were then stored at 4° C. until further processing.

Growth performance of transgenic *Arabidopsis* p35 S-CDS2591 plants under salt stress Seeds harvested from the primarily transformed *Arabidopsis* plants, here referred to as T0 seeds, were used to evaluate growth performance under salt stress. Transgenic T1 plants were compared to the segregant non-transgenic nullizygous plants of the same mother plant, here denominated control plants. The visual marker incorporated into the plants was used to identify transformed and control seeds. To this aim dry seeds were examined under blue light to determine the presence of transformed seeds. 80 bright fluorescent seeds (expressing the transgene) and the same amount of non-fluorescent seeds (not expressing the transgene) seeds were imbibed in 0.2% agar at 4° C. and allowed to germinate in a soil mixture of sand and peat (1:3). At 15 days post imbibition (dpi), a set of 14 individual transgenic and 12 control plants, all in a similar developmental stage, were selected for further analysis and transplanted to soil on pots of 6.5 cm in diameter. Plants were grown in greenhouse conditions (22° C. during the day, 18° C. at night, 60% relative humidity, 20 hour photoperiod, with a sub-irrigation watering). Salt treatment was applied 3 times over a period of 1 week on seedlings of 21 dpi by watering with 150 mM NaCl, and the plants were then allowed to recover by watering with tap water. The plants were photographed weekly and at different angles, using a digital camera over a period of 4 weeks. Images were analysed (the number of pixels corresponding to plant tissues was recorded for each picture), and used for measurement of plant size (plant area and height) using appropriate software.

Results

Figure 8:
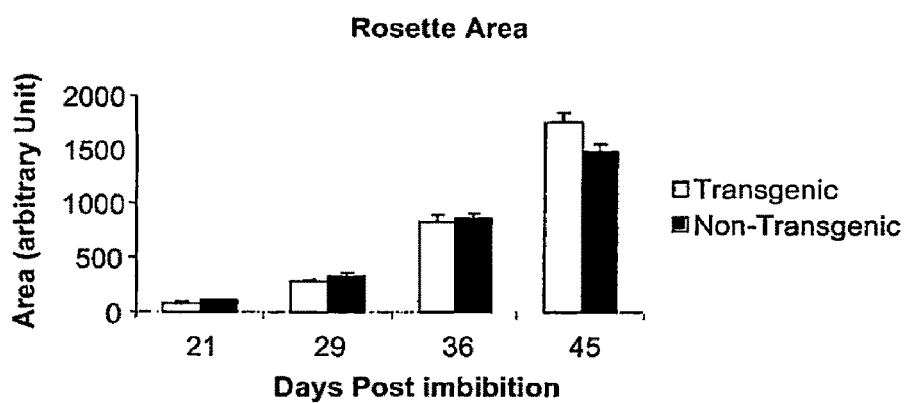
FIG. 8: Rossette Area. Average rosette area for transgenic and control non-transgenic plants is represented in arbitrary units at 4 time points between 21 and 45 dpi. Standard error bars are shown.
Figure 9:
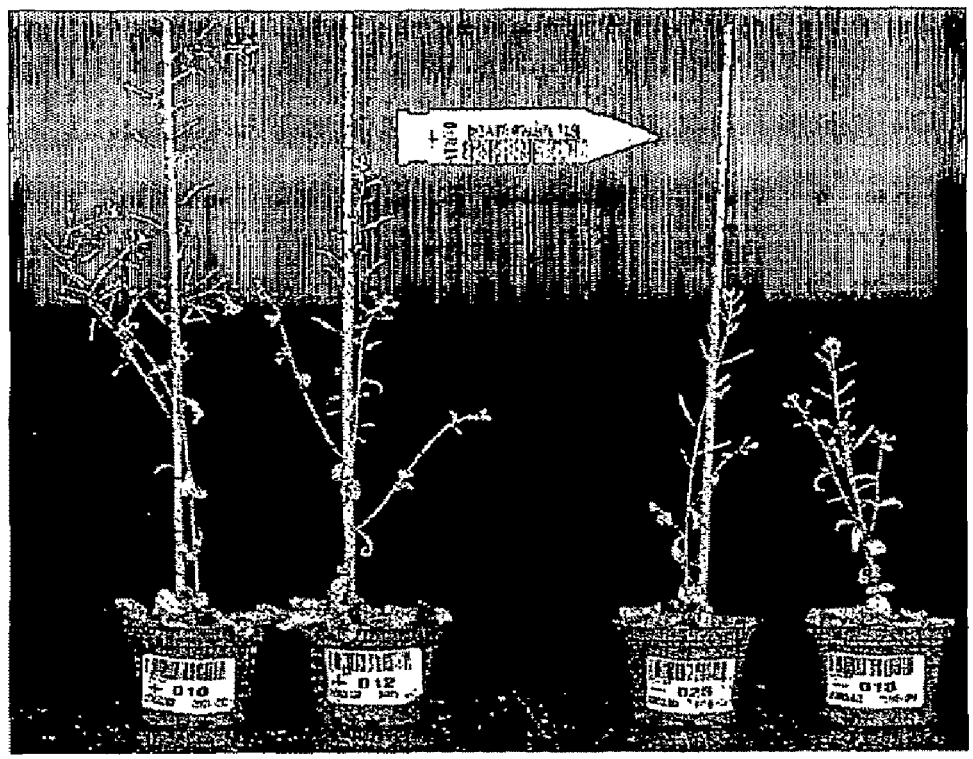
FIG. 9: Transgenic plants (2 plants on the left) and non-transgenic control plants (2 plants in the right) 5 weeks upon recovery from stress (150 mM NaCl). Picture was taken at 54 dpi.

The salt stress applied affected growth of both transgenic and non-transgenic control plants. Transgenic plants showed a better growth recovery from stress as can be derived from FIG. 8. Transgenic plants showed a higher growth rate such that four weeks after recovery from stress treatment the rosette of the transgenic plants was 20% larger than in control plants (Table 2). However, the strongest effect was observed in the development of the inflorescence structures. Non-transgenic plants had a poor inflorescence structure with very few branches, while transgenic plants were able to develop their inflorescence further so that more branches, more flowers, more siliques and presumably more seeds were produced (FIG. 9). Two parameters reflected the development of the inflorescence, 1) Inflorescence height, which is the distance between 2 horizontal lines drawn at the rosette level and the highest point detected for the inflorescence structures and 2) Inflorescence Area, which is the surface of all plant structures detected in the digital images above the rosette level. Values obtained for both parameters reflect the better development of inflorescence structures in transgenic plants and reveals a difference of more than 40% in the inflorescence height and of more than 60% in the total inflorescence area (Table 2).

TABLE 2

Growth performance of transgenic Arabidopsis plants under salt-stress conditions. Rosette area, Inflorescence height, and Inflorescence area are expressed in arbitrary units. The percentage values refer to the difference in transgenic plants (TR) with respect to segregant non-transgenic (NT), taken the values for non transgenic plants as 100. Measurements were done at 45 dpi. The T-test shows the p-value obtained with the student's t-test.

|  | Transgenic | Non-Transgenic | T-test |
| --- | --- | --- | --- |
| Rosette Area | 1787.77 | 1467.62 | 0.0120 |
| Rossette Area (TR/NT) In % | 121.81 | 100 |  |
| Inflorescence heigth | 110.08 | 74.67 | 0.0001 |
| Inflorescence Heigth | 147.42 | 100.00 |  |

TABLE 2-continued

Growth performance of transgenic Arabidopsis plants under salt-stress conditions. Rosette area, Inflorescence height, and Inflorescence area are expressed in arbitrary units. The percentage values refer to the difference in transgenic plants (TR) with respect to segregant non-transgenic (NT), taken the values for non transgenic plants as 100. Measurements were done at 45 dpi. The T-test shows the p-value obtained with the student's t-test.

|  | Transgenic | Non-Transgenic | T-test |
|---|---|---|---|
| (TR/NT) In % Inflorescence Area | 350.31 | 217.83 | 0.0507 |
| Inflorescence Area (TR/NT) In % | 160.81 | 100 | |

Example 8

Growth Performance of Rice Plants Transformed with Plant Non-Symbiotic Haemoglobin Coding Sequences (i) Cloning of Haemoglobin Genes The isolation of *Arabidopsis thaliana* heamoglobin gene 2 (AtHB2, CDS2591), and *Beta vulgaris* haemoglobin gene CDS2767, was described in the previous examples.

For CDS2767 (Xero2), a plasmid containing the corresponding nucleic acid sequence (earlier described) was used as substrate for the PCR. Specific primers for each of the haemoglobin genes, detailed in Table 3, were used in the amplification. In addition to the specific sequences, the forward primers contained the gateway AttB1 site, and the reverse primers the AttB2 site of the Gateway recombination system.

TABLE 3

List Primers.

| PrimerNumber | Description | SEQ ID NO |
|---|---|---|
| prm05458 | attB2 CDS2591 | 7 |
| prm06122 | attB1 CDS2591 | 8 |
| prm06021 | attB1 CDS2767 | 11 |
| prm06022 | attB2 CDS2767 | 12 |

PCR was performed using Hifi Taq DNA polymerase in standard conditions. Specific PCR fragments corresponding to the CDS (Table 4) were isolated and purified using standard procedures. The first step of the Gateway procedure, the BP reaction, was then performed, during which the PCR fragment recombines in vivo with the pDONR201 plasmid to produce, according to the Gateway terminology, an "entry clone". A list of genes used and their corresponding entry clones is given in Table 4.

TABLE 4

List of haemoglobin genes for cloning into rice.

| Internal reference | ORF | Origin Species | Entry Clone name |
|---|---|---|---|
| CDS2591 | AtHB2 | Arabidopsis thaliana | P055 |
| CDS2767 | BvHb | Beta vulgaris | P06289 |

Each entry clone vector thus contains the corresponding CDS within the AttL1 and AttL2 sites for Gateway® cloning in the pDONR201 backbone. This vector contains also a bacterial kanamycin-resistance cassette and a bacterial origin of replication.

(ii) Vector Construction for Rice Transformation

The entry clones listed in Table 4 were subsequently used in an LR reaction with a destination vector (gateway nomenclature) used for rice transformation. This vector contains as functional elements within the T-DNA borders: a plant selectable marker, a screenable marker and a Gateway cassette intended for LR in vivo recombination with the sequence of interest already cloned in the entry done. A plant promoter is located upstream of this Gateway cassette. A description of the destinations vectors used is given in Table 5.

TABLE 5

Destination vectors.

| Destination Vector | Promoter | Description promoter | Expression pattern in rice |
|---|---|---|---|
| P00640 | PRO0129 | Promoter of rice GOS2 gene. | Constitutive |
| P00831 | PRO0218 | GenBank AF019212 nucleotides (1-1256) | Seed: mainly endosperm |
| P05653 | PRO0151 | Promoter of rice wsi18 gene. | Seed: mainly embryo |

After the LR recombination step, the resulting expression vector can be transformed into the *Agrobacterium* strain LBA4404 and subsequently to rice plants since the expression vectors are binary vector for expression in rice of the different CDS under the control of a particular promoter. These vectors contain a T-DNA derived from the Ti Plasmid, limited by a left border (LB repeat, LB Ti C58) and a right border (RB repeat, RB Ti C58)). From the left border to the right border, this T-DNA contains: a selectable marker cassette for selection of transformed plants; a screenable marker cassette for visual screening of transformed plants; the specific plant promotere-CDS of interest and a zein and rbcS-deltaGA double terminator cassette. These vectors also contain an origin of replication from pBR322 for bacterial replication and a selectable marker (Spe/SmeR) for bacterial selection with spectinomycin and streptomycin. The expression vectors generated and the respective genes of interest are described in Table 6. All constructs (1 to 8) are designed for overxpression.

TABLE 6

Plant Transformation Vectors.

| Construct # | Entry done | Destination Vector | Promoter | CDS | GOI |
|---|---|---|---|---|---|
| 1 | P06289 | P00831 | PRO0218 | CDS2767 | BvHB |
| 2 | P06289 | P00640 | PRO0129 | CDS2767 | BvHB |
| 3 | P06289 | P05653 | PRO0151 | CDS2767 | BvHB |
| 4 | P06289 | P05653 | PRO0151 | CDS2591 | AtHB2 |

(iii) Transformation of Rice with Plant Transformation Vectors.

The T-DNA of constructs listed in Table 6 were transformed in rice.

Mature dry seeds of *Oryza sativa* japonica cultivar Nipponbare were dehusked. Sterilization was done by incubating the seeds for one minute in 70% ethanol, followed by 30 minutes in 0.2% $HgCl_2$ and by 6 washes of 15 minutes with sterile distilled water. The sterile seeds were then germinated on a medium containing 2,4-D (callus induction medium). After a 4-week Incubation in the dark, embryogenic, scutellum-derived calli were excised and propagated on the same medium. Two weeks later, the calli were multiplied or propagated by subculture on the same medium for another 2 weeks. 3 days before co-cultivation, embryogenic callus pieces were sub-cultured on fresh medium to boost cell division activity. The *Agrobacterium* strain LBA4404 harbouring the binary vectors (constructs 1 to 8, Table 6), was used for co-cultivation. The *Agrobacterium* strain was cultured for 3 days at 28° C. on AB medium with the appropriate antibiotics. The bacteria were then collected and suspended in liquid co-cultivation medium at an $OD_{600}$ of about 1. The suspension was transferred to a petri dish and the calli were immersed in the suspension during 15 minutes. Next, the callus tissues were blotted dry on a filter paper, transferred to solidified co-cultivation medium and incubated for 3 days in the dark at 25° C. Thereafter, co-cultivated callus was grown on 2,4-D-containing medium for 4 weeks in the dark at 28° C. in the presence of a selective agent at a suitable concentration. During this period, rapidly growing resistant callus islands developed. Upon transfer of this material to a regeneration medium and incubation in the light, the embryogenic potential was released and shoots developed in the next four to five weeks. Shoots were excised from the callus and incubated for 2 to 3 weeks on an auxin-containing medium from which they were transferred to soil. Hardened shoots were grown under high humidity and short days in a greenhouse. Finally seeds were harvested three to five months after transplanting. The method yielded single locus transformants at a rate of over 50% (Aldemita and Hodges, Planta 199, 612-617, 1996; Chan et al., Plant Mol. Biol. 22(3), 491-506, 1993; Hiei et al., Plant J. 6(2), 271-282, 1994).

(iv) Evaluation of Transgenic Rice Transgenic Plants

Approximately 15 to 20 independent T0 rice transformants are generated. The primary transformants are transferred from tissue culture chambers to a greenhouse for growing and harvest of T1 seed. Generally, 5-10 events, of which the T1 progeny segregates 3:1 for presence/absence of the transgene, are retained. For each of these events, approximately 10 T1 seedlings containing the transgene (hetero- and homo-zygotes), and approximately 10 T1 seedlings lacking the transgene (nullizygotes), are selected by monitoring expression of the screenable marker.

Vegetative Growth Measurements

The selected T1 plants (approximately 10 with the transgene and approximately 10 without the transgene) are transferred to a greenhouse. Each plant receives a unique barcode label to link unambiguously the phenotyping data to the corresponding plant. The selected T1 plants are grown on soil in 10 cm diameter pots under the following environmental settings: a photoperiod of 11.5 h, daylight intensity of 30,000 lux or more, daytime temperature of 28° C. or higher, night time temperature of 22° C., relative humidity between 60-70%. Transgenic plants and the corresponding nullizygotes are grown side-by-side at random positions. From the stage of sowing until the stage of maturity each plant are passed several times through a digital imaging cabinet and imaged. At each time point digital images (2048×1536 pixels, 16 million colors) are taken of each plant from at least 6 different angles. Also, pictures are taken from each of the approximately ten selected transgenic plants with the transgene and also from each of the selected plants not containing the transgene. One or more of the parameters described below can be derived in an automated way from the all the digital images of all the plants, using image analysis software.

(a) Aboveground Plant Area

Plant above ground area is determined by counting the total number of pixels from aboveground plant parts discriminated from the background. This value is averaged for the pictures taken on the same time point from the different angles and is converted to a physical surface value expressed in square mm by calibration. Experiments show that the aboveground plant area measured this way correlates with the biomass of plant parts above ground.

(b) Plant Height

Plant height is determined by measuring the distance between the horizontal lines going through the upper pot edge and the uppermost pixel corresponding to a plant part above ground. This value is averaged for the pictures taken on the same time point from the different angles and is converted, by calibration, to a physical distance expressed in mm. Experiments showed that plant height measured this way correlate with plant height measured manually with a ruler.

(c) Number of Tillers

The number of primary tillers is manually counted at the harvesting of the plants. The tillers are cut off at 3 cm above the pot rim. They are then counted at the cut surface. Tillers that are together in the same sheath are counted as one tiller.

(d) Number of Primary Panicles

The tallest panicle and all the panicles that overlap with the tallest panicles when aligned vertically are counted manually, and considered as primary panicles.

(e) Number of Secondary Panicles

The number of panicles that remain on the plant after the harvest of the primary panicles is counted and considered as secondary panicles.

(f) Growth Curve

The weekly measurements of the plant area are modelled to obtain a growth curve for each plant, plotted as the value of plant area (in $mm^2$) over the time (in days). From this growth curve the following parameters can be calculated:

(g) A42

A42 is the plant area at day 42 after sowing as predicted by the growth curve model.

(h) Tmid

Tmid is the time that a plant needs to grow and reach 50% of the maximum plant area. Tmid is predicted from the growth curve model.

(i) T90

T90 is the time that a plant needs to grow and reach 90% of the maximum plant area. T90 is predicted from the growth curve model.

Seed-Related Parameter Measurements

The mature primary panicles are harvested, bagged, barcode-labelled and then dried for three days in the oven at 37° C. The panicles are then threshed and all the seeds are collected and counted. The filled husks are separated from the empty ones using an air-blowing device. The empty husks are discarded and the remaining fraction is counted again. The filled husks are weighed on an analytical balance. This procedure results in the set of seed-related parameters described below.

(a) Total Seed Number Per Plant

Total seed number per plant is measured by counting the number of husks harvested from a plant (b) Number of Filled Seeds:

Number of filled seeds is determined by counting the number of filled husks that remaine after the separation step.

(c) Total Seed Yield Per Plant

The total seed yield is measured by weighing all filled husks harvested from a plant.

(d) Harvest Index of Plants

The harvest index in the present invention is defined as the ratio between the total seed yield and the above ground area ($mm^2$), multiplied by a factor $10^6$.

(e) Thousand Kernel Weight (TKW) of Plants

This parameter is extrapolated from the number of filled seeds counted, and their total weight.

(f) TotalArea Emergence Prop.

Is the time when the plant reaches 30% of its maximal total area (g) TotalArea Cycle Time.

Is the time when the plant reaches 90% of its maximal total area (v) Statistical Analysis: T-Test and F-Test A two-factor ANOVA (analysis of variants) is used as statistical model for the overall evaluation of plant phenotypic characteristics. An F-test is carried out on all the parameters measured of all the plants of all the events transformed with the gene of the present invention. The F-test is carried out to check for an effect of the gene over all the transformation events and to verify for an overall effect of the gene, also named herein "global gene effect". If the value of the F test shows that the data are significant, than it is concluded that there is a "gene" effect, meaning that not only presence or the position of the gene is causing the differences in phenotype. The threshold for significance for a true global gene effect is set at 5% probability level for the F test.

To check for an effect of the genes within an event, i.e., for a line-specific effect, a t-test is performed within each event using data sets from the transgenic plants and the corresponding null plants. "Null plants" or "Null segregants" are the plants treated in the same way as the transgenic plant, but from which the transgene has segregated. Null plants can also be described as the homozygous negative transformants. The threshold for significance for the t-test is set at 10% probability level. Within one population of 5 transformation events, some events can be under or above this t-test threshold. This is based on the hypothesis that a gene might only have an effect in certain positions in the genome, and that the occurrence of this position-dependent effect is not uncommon. This kind of gene effect is also named herein a "line effect of the gene".

The p value is obtained by comparing the t value to the t distribution or alternatively, by comparing the F value to the F distribution. The p value then stands for the probability that the null hypothesis (null hypothesis being "there is no effect of the transgene") is correct.

(vi) Specific Growth Conditions.

Growth of the plants takes place in the greenhouse as described earlier, either under optimal or sub-optimal conditions. Under optimal conditions the plants are watered regularly with a nutrient solution containing N:P:K 20:20:20 at a final conductivity of EC=1.1 mS.

Two type of sub-optimal conditions are used:

1—Salt Stress.

The nutrient solution is supplemented with NaCl to 15 mM. The saline solution is applied to the plants from 3 weeks after sowing till the time of harvest.

2—Drought Stress.

Plants are grown and watered with a frequency optimal for growth such that no signs of excess or deficit of watered are visible, till heading stage. When about 50% of the control non-transgenic plants for a particular construct reach the end of tillering and panicles start to form at heading stage (end of stage V9 to R0 stage as defined by Counce et al. 2000), all plants (transgenic and non-transgenic) belonging that particular construct are watered till the pots contain 60% RWC (relative water content), then water is withheld till the RWC drops to 20% (most control plants show a rolling index of 4). Rewatering to normal optimal frequency is then resumed Transgenic plants showing improved values from an agronomical point of view, for a biomass or seed parameter measured in the greenhouse, are selected for further testing in field conditions.

The invention claimed is:

1. Method for producing plants with at least one altered plant characteristic selected from increased yield, increased biomass, altered architecture and altered cell division of the plant compared to a control plant, said method comprising increasing expression in plants of a nucleic acid sequence encoding plant class-2 non-symbiotic haemoglobin by transforming said plants with a nucleic acid sequence encoding plant class-2 non-symbiotic haemoglobin to produce transformed plants, said nucleic acid sequence being SEQ ID NO:3 or a nucleic acid sequence encoding the amino acid sequence of SEQ ID NO:4, wherein the plant characteristic is selected from one or more of increased yield, increased biomass, altered architecture or altered cell division, and selecting from the transformed plants those transformed plants which have at least one of said characteristics.

2. Method of claim 1, wherein said increased yield comprises increased seed yield.

* * * * *